(12) United States Patent
Jakobovits et al.

(10) Patent No.: US 6,235,883 B1
(45) Date of Patent: May 22, 2001

(54) HUMAN MONOCLONAL ANTIBODIES TO EPIDERMAL GROWTH FACTOR RECEPTOR

(75) Inventors: Aya Jakobovits, Menlo Park; Xiao-Dong Yang, Palo Alto; Michael Gallo, San Jose; Xiao-Chi Jia, San Mateo, all of CA (US)

(73) Assignee: Abgenix, Inc., Fremont, CA (US)

( * ) Notice: Subject to any disclaimer, the term of this patent is extended or adjusted under 35 U.S.C. 154(b) by 0 days.

(21) Appl. No.: 08/851,362

(22) Filed: May 5, 1997

(51) Int. Cl.[7] .................................................. C07K 16/28
(52) U.S. Cl. .............................. 530/388.22; 530/387.3; 530/388.1; 530/388.15; 530/387.7; 424/133.1; 424/138.1; 424/139.1; 424/142.1
(58) Field of Search .............................. 530/387.9, 387.3, 530/387.7, 388.22, 388.15, 388.1; 424/133.1, 138.1, 143.1, 142.1, 139.1, 141.1

(56) References Cited

FOREIGN PATENT DOCUMENTS 586 002 A2 * 8/1993 (EP).
712 863 A1 * 5/1996 (EP).

OTHER PUBLICATIONS

Klein, J., Immunolgy: The Science of Self–Nonself Discrimination, John Wiley & Sons: New York, NY, p. 176, 1982.*

Schulz et al., Principles of Protein Structure, Springer–Verlag: New York, NY, pp. 14–16, 1979.*

Modjtahedi et al., The receptor for EGF and its ligand: expression, prognostic value and target for therapy in cancer (Review), Int. J. Oncol., 4: 277–296, 1994.*

GenBank Accession No. Z70619, *H. sapiens* mRNA for immunoglobulin heavy chain variable regions (6D4–A5, VH4, 4–31/DP–65), accessed Dec. 3, 1998, May 1996.*

GenBank Accession No. Z70658, *H. sapiens* mRNA for immunoglobulin heavy chain variable regions (83–6H3, VH4, 4–61/DP–66), accessed Dec. 3, 1998, May 1996.*

* cited by examiner

*Primary Examiner*—Lorraine Spector
*Assistant Examiner*—Claire M. Kaufman
(74) *Attorney, Agent, or Firm*—Christopher A. Hare

(57) ABSTRACT

In accordance with the present invention, there are provided fully human monoclonal antibodies against human epidermal growth factor receptor (EGF-r). Nucletide sequences encoding and amino acid sequences comprising heavy and light chain immunoglobulin molecules, particularly sequences corresponding to contiguous heavy and light chain sequences from CDR1 through CDR3, are provided. Hybridomas expressing such immunoglobulin molecules and monoclonal antibodies are also provided.

16 Claims, 20 Drawing Sheets

VSGGSN SG DYYWS WIRQHPGKGL DC IGYIYYSGSTYYNPSLKSRVTISVDTSKNQF LKL T SVTAADTAVYYCARSTVVNPGWFDPWGQGTLVTVSS (SEQ ID NO: 23)
    CDR1                      CDR2                                                     CDR3

FIG. 1

GTCTCTGGTG GCTCCATCAA CAGTGGTGAT TACTACTGGA GCTGGATCCG CCAGCACCCA GGGAAGGGCC TGGACTGCAT TGGGTACATC TATTACAGTG GGAGCACCTA CTACAACCCG
TCCCTCAAGA GTCGAGTTAC CATATCAGTA GACACGTCTA AGAATCAGTT CTTCCTGAAG CTGACCTCTG TGACTGCCGC GGACACGGCC GTGTATTACT GTGCGAGATC TACGGTGGTA
AATCCGGGGT GGTTCGACCC CTGGGGCCAR GGAACCCTGG TCACCGTCTC CTCA (SEQ ID NO: 3)

FIG. 2

TITCQASQDI N NYLNW F QQKPGKAPK VLI H DASNLETG G PSRFSGSGSGTDFTFTIS G LQPEDIATYYCQQY E S LPLTFGGGTKVEIKRTVAAPSVFIFPPSDEQ (SEQ ID NO: 24)
          CDR1                        CDR2                                           CDR3

FIG. 3

ACCATCACTT GCCAGGCGAG TCAGGACATT AACAACTATT TAAATTGGTT TCAGCAGAAA CCAGGGAAAG CCCCT AAGGTCCTGA TCCACGATGC TCCACGATGC GAAACAGGGG
GCCCATCAAG GTTCAGTGGA AGTGGATCTG GGACA GATTTACTT TCACCATCAG CGGCCTGCAG CCTGAAGACA TTGCAACATA TTATTGTCAA CAGTATGAAA GTCTC CCACTCACTT
TCGGCGGAGG GACCAAGGTG GAGATCAAA (SEQ ID NO: 4)

FIG. 4

VSGGSINSGDYYWSWIRQHPGKGLEWIGSIYYSGNTFYNPSLKSRVTISLDTSKNQFSLKLSSVTAADTAVCYCARNIVTTGAFDIWGQGTMVTVSS (SEQ ID NO: 25)
 CDR1                       CDR2                                                    CDR3

FIG. 5

GTCTCTGGTG GCTCCATCAA CAGTGGTGAT TACTACTGGA GCTGGATCCG CCAGCACCCA GGGAAGGGCC TGGAGTGGAT TGGTCCATC TATTACAGTG GAACACCTT CTACAACCCG
TCCCTCAAGA GTCGAGTTAC CATATCACTA GACACGTCTA AGAACCAGTT CTCCCTGAAG CTGAGTTCTG TGACTGCCGC GGACACGGCC GTGTGTTACT GTGCGAGAAA TATAGTGACT
ACGGGTGCTT TTGATATCTG GGGCCAAGGG ACAATGGTCA CCGTCTCTTC A (SEQ ID NO: 5)

FIG. 6

TITCQASQDITIYLNWYQQKPGKAPKLLINDASSLETGVPLRFSGSGSGTDFTFTISSLQPEDIATYYCQQYDHLPLTFGGGTKVAIKRTVAAPSVFIFPPSDEQ (SEQ ID NO: 26)
 CDR1                    CDR2                                              CDR3

FIG. 7

ACCATCACTT GTCAGGCGAG TCAGGACATT ACCATTTATT TAAATTGGTA TCAACAGAAA CCAGGGAAAG CCCCT AAGCTCCTGA TCAACGACGC ATCCAGTTTG GAAACAGGGG
TCCCATTAAG GTTCAGTGGA AGTGGATCTG GGACA GATTTACTT TCACCATCAG CAGCCTGCAG CCTGAAGATA TTGCAACATA TTACTGTCAA CAGTATGATC ATCTC CCGCTCACTT
TCGGCGGGCG GACCAAGGTG GCGATCAAA (SEQ ID NO: 6)

FIG. 8

VSGGSISSSGDYYWTWIRQHPGKGLEWIGYIYYSGNTYYNPSLKSRVSMSIDTSENQFSLKLSSVTAADTAVYYCARKPVTGGEDYWGQGTLVTVSS (SEQ ID NO: 27)
    CDR1                        CDR2                                              CDR3

FIG. 9

GTCTCTGGTG GCTCCATCAG CAGTGGTGAT TACTACTGGA CCTGGATCCG CCAGCACCCA GGGAAGGGCC TGGAGTGGAT TGGGTACATC TATTACAGTG GGAACACCTA CTACAACCCG
TCCCTCAAGA GTCGAGTTTC CATGTCAATA GACACGTCTG AGAACCAGTT CTCCCTGAAG CTGAGCTCTG TGACTGCCGC GGACACGGCC GTGTATTACT GTGCGAGAAA ACCAGTGACT
GGGGGGAGG ACTACTGGGG CCAGGGAACC CTGGTCACCG TCTCCTCA (SEQ ID NO: 7)

FIG. 10

TITCQASQDISNYLNWYQQKPGKAPKLLIYDASNLETGVPSRFSGSGSGTDFTFTISSLQPEDIVGYYVQQYESLPCGFGQGTKLEIKRTVAAPSVFIFPPSDEQ (SEQ ID NO: 28)
    CDR1                      CDR2                                                            CDR3

FIG. 11

ACCATCACTT GCCAGGCGAG TCAGGACATT AGTAACTATT TAAATTGGTA TCAGCAGAAA CCAGGGAAAG CCCT AAGCTCCTGA TCTACGATGC TTCCAATTTG GAAACAGGGG TCCCATCAAG
GTTCAGTGGA GTGGATCTG GGACA GATTTTACTT TCACCATCAG CAGCCTGCAG CCTGAAGATA TTGGAACATA TGTCTGTCAA CAGTATGAGA GTCTC CCGTGCGGTT TTGGCCAGGG
GACCAAACTG GAGATCAAA (SEQ ID NO: 8)

FIG. 12

VSGGSINSGDFYWSWIRQHPGKGLEWIGYIYYSGSTYYNPSLKSRVTMSIDPSKNQFSLKLISVTAADTAVYYCATSLYYGGMDVWGQGTTVTVSS (SEQ ID NO: 29)
　　　　　CDR1　　　　　　　　　　　　CDR2　　　　　　　　　　　　　　　　　　　　　　　　CDR3

FIG. 13

GTCTCTGGTG GCTCCATCAA CAGTGGTGAT TTCTACTGGA GCTGGATCCG CCAACACCCA GGGAAGGGCC TGGAGTGGAT TGGGTACATC TATTACAGTG GGAGCACCTA CTACAACCCG
TCCCTCAAGA GTCGAGTTAC CATGTCAATA GACCCGTCTA AGAACCAGTT CTCCCTGAAA CTGATCTCTG TGACTGCCGC GGACACGGCC GTTTATTACT GTGCGACNTC CCTTTACTAT
GGCGGGGGTA TGGACGTCTG GGGCCAAGGG ACCACGGTCA CCGTCTCCTC A (SEQ ID NO: 9)

FIG. 14

TITCQASQDISNNLNWYQQKRGNAPKLLIYDASNLETGVPSRFSGSGSGTDFTFTISNLQPEDIATYYCQHYDHLPWTFGQGTKVEXKRTVAAPSVFIFPPSDEQ (SEQ ID NO: 30)
　　　　CDR1　　　　　　　　　　　　　　CDR2　　　　　　　　　　　　　　　　　　　　　　　　　　CDR3

FIG. 15

ACCATCACTT GCCAGGCGAG TCAGGACATT AACAACTATT TGAATTGGTA TCAGCAGAGG CCNGGGAACG CCCCT AAACTCCTGA TCTACGATGC ATCCAATTTG GAAACAGGGG
TCCCATCAAG GTTCAGTGGA AGTGGATCTG GGACA GATTTACTT TCACCATCAA CAGCCTGCAG CCTGAAGATA TTGCGACATA TTATTGTCAA CACTATGATC ATCTC CCGTGGACGT
TCGGCCAAGG GACCAAGGTG GAANTCAAA (SEQ ID NO: 10)

FIG. 16

VSGGSINNGDYYWSWIRQHPGKGLEWIGHIYYSGSTYYIPSLKSRTTISVDTSKNQFSLKLNSVTAADTAVYYCARGTVTTYYFDYWGQGTTVTVSS (SEQ ID NO: 31)
          CDR1                    CDR2                              CDR3

FIG. 17

GTCTCTGGTG GCTCCATCAA CAATGGTGAT TACTACTGGA GCTGGATCCG CCAGCACCCA GGGAAGGGCC TGGAGTGGAT TGGGCACATC TATTACAGTG GGAGCACCTA CTACATCCCG
TCCCTCAAGA GTCGAGTCAC CATATCAGTA GACACGTCTA AGAACCAGTT CTCCCTGAAG CTGAACTCTG TGACTGCCGC GGACACGGCC GTGTATTACT GTGCGAGAGG GACAGTAACT
ACGTACTACT TTGACTACTG GGGCCAGGGA ACCCTGGTCA CCGTCTCCTC A (SEQ ID NO: 11)

FIG. 18

TITCRASQSISSYLNWYQQKPGKAPKLLIYAASSLQSGVPSRFSGSGSGTDFTLTISSLQPEDFATYYCQQGYRTPPECSFGQGTKLEIKRTVAAPSVFIFPPSDEQ (SEQ ID NO: 32)
      CDR1                     CDR2                              CDR3

FIG. 19

ACCATCACTT GCCGGGCAAG TCAGAGCATT AGCAGCTATT TAAATTGGTA TCAGCAGAAA CCAGGGAAAG CCCCT AAGCTCCTGA TCTATGCTGC ATCCAGTTTG CAAAGTGGGG
TCCCATCAAG GTTCAGTGGC AGTGGATCTG GGACA GATTTCACTC TCACCATCAG CAGTCTGCAA CCTGAAGATT TTGCAACTTA CTACTGTCAA CAGGGTTACA GAACC CCTCCGGAGT
GCAGTTTTGG CCAGGGGACC AAGCTGGAGA TCAAA (SEQ ID NO: 12)

FIG. 20

VSGGSVSSG<u>D</u>YYWSWIRQPPGKGLEWIG<u>HL</u>YYSG<u>N</u>TNYNPSLKSRVTIS<u>L</u>DTSKNQFSLKLSSVTAADTAVYYCAR<u>DFLTGSFFDY</u>WGQGTLVTVSS (SEQ ID NO: 33)

CDR1         CDR2                    CDR3

FIG. 21

GTCTCTGGTG GCTCCGTCAG CAGTGGTGAT TACTACTGGA GCTGGATCCG GCAGCCCCCA GGGAAGGGAC TGGAGTGGAT TGGACATCTC TATTACAGTG GGAACACCAA CTACAACCCC
TCCCTCAAGA GTCGAGTCAC CATATCATTA GACACGTCCA AGAACCAGTT CTCCCTGAAG CTGAGCTCTG TGACCGCTGC GGACACGGCC GTGTATTACT GTGCGAGAGA TTTTTTGACT
GGTTCCTTCT TTGACTACTG GGGCCAGGGA ACCCTGGTCA CCGTCTCCTC A (SEQ ID NO: 13)

FIG. 22

TITCQAS<u>Q</u>DISNYLNWYQQKPGKAPKLLI<u>N</u>DAS<u>D</u>LETGVPSR<u>I</u>SGSGSGTDFTFTIS<u>N</u>LQPEDIATYYCQQY<u>D</u><u>SLPLT</u>FGGGTKVEIRRTVAAPSVFIFPPSDEQ (SEQ ID NO: 34)

CDR1             CDR2                   CDR3

FIG. 23

ACCATCACTT GCCAGGCGAG TCAGGACATA AGCAACTATT TAAATTGGTA TCAGCAGAAA CCAGGGAAAG CCCCT AAGCTCCTGA TCAACGATGC TCAAGCTCCT GA TCAACGATGC ATCCGATTTG GAAACAGGGG
TCCCATCAAG GATCAGTGGA AGTGGATCTG GGACA GATTTTACTT TCACCATCAG CAACCTGCAG CCTGAAGATA TTGCAACATA TTACTGTCAA CAATATGATA GTCTC CCGCTCACTT
TCGGCGGAGG GACCAAGGTG GAGATCAGA (SEQ ID NO: 14)

FIG. 24

VSGGSV YSG DYYWS WIRQPPGKGLEWIGYIYYSGSTNYNPSLKSRVTISVDTSKNQFSLKLSSVTAADTAVYYCARDSILGATNYWGQGTLVTVSS (SEQ ID NO: 35)
         <u>CDR1</u>                       <u>CDR2</u>                                       <u>CDR3</u>

FIG. 25

GTCTCTGGTG GCTCCGTCTA CAGTGGTGAT TACTACTGGA GCTGGATCCG GCAGCCCCCC GGGAAGGGAC TGGAGTGGAT TGGGTATATC TATTACAGTG GGAGCACCAA TTACAATCCC
TCCCTCAAGA GTCGAGTCAC CATATCAGTA GACACGTCCA AGAACCAGTT CTCCCTGAAG CTGAGCTCTG TGACCGCTGC GGACACGGCC GTGTATTACT GTGCGAGAGA CTCCATACTG
GGAGCTACCA ACTACTGGGG CCAGGGAACC CTGGTCACCG TCTCCTCA (SEQ ID NO: 15)

FIG. 26

TITCQASQ X ISNYL X WYQQKPGKAPK X LIS DASNLETGVPSRFSGSGSGT X X TFTISSLQPEDIATY HC X QY X SLPLTFGGGTKVEIKRTVAAPSVFIFPPSDEQ (SEQ ID NO: 36)
           <u>CDR1</u>                       <u>CDR2</u>                                       <u>CDR3</u>

FIG. 27

ACCATCACTT GCCAGGCGAG TCNGGACATT AATAACTATT TANATTGGTN TCAGCAGAAA CCAGGGAAAG CCCCT AAASTCCTGA TCTCCGATGC ATCCAATTTA GAAACAGGGG
TCCCATCGAG GTTCAGTGGA AGTGGATCTG GGACA GANTNTACTT TCACCATCAG CAGCCTGCAG CCTGAAGATA TTGCNACATA TCACTGTCNA CAGTATNATA GTCTC CCGCTCACTT
TCGGCGGAGG GACCAAGGTA GAGATCAAA (SEQ ID NO: 16)

FIG. 28

VSGGSVSSGDYYWTWIRQSPGKGLEWIGHIYYSGNTNYNPSLKSRLTISIDTSKTQFSLKLSSVTAADTAIYCVRDRVTGAFDIWGQGTMVTSS (SEQ ID NO: 37)
                    ‾‾‾‾‾                  ‾‾‾‾‾‾‾‾‾‾‾‾‾‾‾‾‾‾                          ‾‾‾‾‾‾‾‾‾‾‾‾
                    CDR1                   CDR2                                       CDR3

FIG. 29

GTCTCTGGTG GCTCCGTCAG CAGTGGTGAT TACTACTGGA CCTGGATCCG GCAGTCCCA GGGAAGGGAC TGGAGTGGAT TGGACACATC TATTACAGTG GGAACACCAA TTATAACCCC
TCCCTCAAGA GTCGACTCAC CATATCAATT GACACGTCCA AGACTCAGTT CTCCCTGAAG CTGAGTTCTG TGACCGCTGC GGACACGGCC ATTTATTACT GTGTGCGAGA TCGAGTGACT
GGTGCTTTTG ATATCTGGGG CCAAGGGACA ATGGTCACCG TCTCTTCA (SEQ ID NO: 17)

FIG. 30

TITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQ (SEQ ID NO: 38)
       ‾‾‾‾‾‾‾‾‾‾‾‾                ‾‾‾‾‾‾‾                                  ‾‾‾‾‾‾‾‾‾‾‾‾
       CDR1                         CDR2                                     CDR3

FIG. 31

ACCATCACTT GCCAGGCGAG TCAGGACATC AGCAACTATT TAAATTGGTA TCAGCAGAAA CCAGGGAAAG CCCCT AAACTCCTGA TCTACGATGC ATCCAATTTG GAAACAGGGG
TCCCATCAAG GTTCAGTGGA AGTGGATCTG GGACA GATTTACTT TCACCATCAG CAGCCTGCAG CCTGAAGATA TTGCAACATA TTTCTGTCAA CACTTTGATC ATCTC CCGCTCGCTT
TCGGCGGAGG GACCAAGGTG GAGATCAAA (SEQ ID NO: 18)

FIG. 32

Inhibition of Human Epidermoid Carcinoma
Formation in Nude Mice by ABX-EGF

| Treatment | Dose (mg) | Tumor Formation[b] (incidence) | Tumor size[c] (cm³) |
|---|---|---|---|
| PBS | 1 | 6/6 | 1.376 |
| Human IgG2[a] | 1 | 6/6 | 1.727 |
| E7.6.3 | 0.2 | 0/5 | 0 |
| | 1 | 0/4 | 0 |
| E2.5 | 0.2 | 0/3 | 0 |
| | 1 | 0/3 | 0 |
| E1.1 | 1 | 0/3 | 0 |

[a] control human myeloma IgG2
[b] incidence determined 19 days post tumor inoculation
[c] tumor size measured 19 days post tumor inoculation

FIG. 41

HUMAN MONOCLONAL ANTIBODIES TO EPIDERMAL GROWTH FACTOR RECEPTOR

BACKGROUND OF THE INVENTION

1. Summary of the Invention

In accordance with the present invention, there are provided fully human contiguous heavy and light chain sequences spanning the complementarity determining regions monoclonal antibodies against human epidermal growth factor receptor (EGF-r). Nucelotide sequences encoding and amino acid sequences comprising heavy and light chain immunoglobulin molecules, particularly sequences corresponding to (CDR's), specifically from CDR1 through CDR3, are provided. Hybridomas expressing such immunoglobulin molecules and monoclonal antibodies are also provided.

2. Background of the Technology

EGF-r has been demonstrated to be overexpressed on many types of human solid tumors. Mendelsohn *Cancer Cells* 7:359 (1989), Mendelsohn *Cancer Biology* 1:339–344 (1990), Modjtahedi and Dean *Int'l J. Oncology* 4:277–296 (1994). For example, EGF-r overexpression has been observed in certain lung, breast, colon, gastric, brain, bladder, head and neck, ovarian, and prostate carcinomas. Modjtahedi and Dean *Int'l J. Oncology* 4:277–296 (1994). Both epidermal growth factor (EGF) and transforming growth factor-alpha (TGF-α) have been demonstrated to bind to EGF-r and to lead to cellular proliferation and tumor growth.

Thus, certain groups have proposed that antibodies against EGF, TGF-α, and EGF-r may be useful in the therapy of tumors expressing or overexpressing EGF-r. Mendelsohn *Cancer Cells* 7:359 (1989), Mendelsohn *Cancer Biology* 1:339–344 (1990), Modjtahedi and Dean *Int'l J. Oncology* 4:277–296 (1994), Tosi et al. *Int'l J. Cancer* 62:643–650 (1995). Indeed, it has been demonstrated that anti-EGF-r antibodies while blocking EGF and TGF-α binding to the receptor appear to inhibit tumor cell proliferation. At the same time, however, anti-EGF-r antibodies have not appeared to inhibit EGF and TGF-α independent cell growth. Modjtahedi and Dean *Int'l J. Oncology* 4:277–296 (1994).

In view of these findings, a number of murine and rat monoclonal antibodies against EGF-r have been developed and tested for their ability inhibit the growth of tumor cells in vitro and in vivo. Modjtahedi and Dean *Int'l J. Oncology* 4:277–296 (1994). The antibody that has apparently advanced the farthest in the clinic is a chimeric antibody, designated C225, which has a murine variable region and a human IgG1 constant region. Modjtahedi and Dean *Int'l J. Oncology* 4:277–296 (1994). The murine antibody, designated 225, upon which the C225 antibody is based, was developed by University of California and Rorer. See U.S. Pat. No. 4,943,533 and European Patent No. 359,282, the disclosures of which are hereby incorporated by reference. The C225 antibody was demonstrated to inhibit EGF-mediated tumor cell growth in vitro and inhibit human tumor formation in vivo in nude mice. The antibody, moreover, appeared to act in synergy with certain chemotherapeutic agents to eradicate human tumors in vivo in xenograft mouse models. Modjtahedi and Dean *Int'l J. Oncology* 4:277–296 (1994).

ImClone has been conducting human clinical trials using the anti-EGF-r antibody designated C225. Phase I and Phase I/II clinical trials in patients with head and neck, prostate, and lung carcinomas apparently have been, or are currently being, conducted with C225. In Phase I clinical trials, no toxicity was detected with multiple injections and with doses of up to perhaps 400 mg/m$^2$, even in cases involving immuno compromised patients. Such studies were conducted as dose escalation studies comprising 5 doses of from about 5 to about 200 mg/m$^2$ and were performed in combination with chemotherapy (i.e., doxorubicin, adriamycin, taxol, and cisplatin). In addition to the apparent safety data that has been generated in these studies, preliminary results from the studies appear to indicate some evidence of tumor shrinkage in 80% of patients having prostate cancer.

Each of these above-mentioned antibodies, however, possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one could introduce human antibody function into a rodent so that the rodent would produce fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs)—an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse™ strains as published in 1994. See Green et al. *Nature Genetics* 7:13–21 (1994). The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. *Nature Genetics* 15:146–156 (1997) and U.S. patent application Ser. No. 08/759,620, filed Dec. 3, 1996, the disclosures of which are hereby incorporated by reference.

Such approach is further discussed and delineated in U.S. patent application Ser. Nos. 07/466,008, filed Jan. 12, 1990, 07/610,515, filed Nov. 8, 1990, 07/919,297, filed Jul. 24, 1992, 07/922,649, filed Jul. 30, 1992, filed 08/031,801, filed Mar. 15, 1993, 08/112,848, filed Aug. 27, 1993, 08/234,145, filed Apr. 28, 1994, 08/376,279, filed Jan. 20, 1995, 08/430,938, Apr. 27, 1995, 08/464,584, filed Jun. 5, 1995, 08/464,582, filed Jun. 5, 1995, 08/463,191, filed Jun. 5, 1995, 08/462,837, filed Jun. 5, 1995, 08/486,853, filed Jun. 5, 1995, 08/486,857, filed Jun. 5, 1995, 08/486,859, filed Jun. 5, 1995, 08/462,513, filed Jun. 5, 1995, 08/724,752, filed Oct. 2, 1996, and 08/759,620, filed Dec. 3, 1996. See also Mendez et al. *Nature Genetics* 15:146–156 (1997). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and PCT Application No. PCT/US96/05928, filed Apr. 29, 1996. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806 and 5,625,825, both to Lonberg and Kay, and GenPharm International U.S. patent application Ser. Nos. 07/574,748, filed Aug. 29, 1990, 07/575,962, filed Aug. 31, 1990, 07/810,279, filed Dec. 17, 1991, 07/853,408, filed Mar. 18, 1992, 07/904,068, filed Jun. 23, 1992, 07/990,860, filed Dec. 16, 1992, 08/053,131, filed Apr. 26, 1993, 08/096,762, filed Jul. 22, 1993, 08/155,301, filed Nov. 18, 1993, 08/161,739, filed Dec. 3, 1993, 08/165,699, filed Dec. 10, 1993, 08/209,741, filed Mar. 9, 1994, the disclosures of which are hereby incorporated by reference. See also International Patent Application Nos. WO 94/25585, published Nov. 10, 1994, WO 93/12227, published Jun. 24, 1993, WO 92/22645, published Dec. 23, 1992, WO 92/03918, published Mar. 19, 1992, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), the disclosures of which are hereby incorporated by reference in their entirety.

The inventors of Surani et al., cited above and assigned to the Medical Research Counsel (the "MRC"), produced a transgenic mouse possessing an Ig locus through use of the minilocus approach. The inventors on the GenPharm International work, cited above, Lonberg and Kay, following the lead of the present inventors, proposed inactivation of the endogenous mouse Ig locus coupled with substantial duplication of the Surani et al. work.

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Human anti-mouse antibody (HAMA) responses have led the industry to prepare chimeric or otherwise humanized antibodies. While the C225 antibody is a chimeric antibody, having a human constant region and a murine variable region, it is expected that certain human anti-chimeric antibody (HACA) responses will be observed, particularly in chronic or multi-dose utilizations of the antibody.

Thus, it would be desirable to provide fully human antibodies against EGF-r that possess similar or enhanced activities as compared to C225 in order to vitiate concerns and/or effects of HAMA or HACA response.

BRIEF DESCRIPTION OF THE DRAWING FIGURES

FIG. 1 is an amino acid sequence of a heavy chain immunoglobulin molecule that is secreted by the hybridoma E1.1. Differences between the sequence encoded by heavy chain variable gene 4-31 and the sequence of the E1.1 secreted heavy chain are indicated in bold and enlarged font. The contiguous sequence from CDR1 through CDR3 is indicated by underlining and CDR1, CDR2, and CDR3 sequences are each indicated by double underlining.

FIG. 2 is a nucleotide sequence of the cDNA encoding the heavy chain immunoglobulin molecule of FIG. 1 that was cloned out of the hybridoma E1.1.

FIG. 3 is an amino acid sequence of a kappa light chain immunoglobulin molecule that is secreted by the hybridoma E1.1. Differences between the sequence encoded by light chain variable gene 018 and the sequence of the E1.1 secreted light chain are indicated in bold and enlarged font. The contiguous sequence from CDR1 through CDR3 is indicated by underlining and CDR1, CDR2, and CDR3 sequences are each indicated by double underlining.

FIG. 4 is a nucleotide sequence of the cDNA encoding the kappa light chain immunoglobulin molecule of FIG. 3 that was cloned out of the hybridoma E1.1.

FIG. 5 is an amino acid sequence of a heavy chain immunoglobulin molecule that is secreted by the hybridoma E2.4. Differences between the sequence encoded by heavy chain variable gene 4-31 and the sequence of the E2.4 secreted heavy chain are indicated in bold and enlarged font. The contiguous sequence from CDR1 through CDR3 is indicated by underlining and CDR1, CDR2, and CDR3 sequences are each indicated by double underlining.

FIG. 6 is a nucleotide sequence of the cDNA encoding the heavy chain immunoglobulin molecule of FIG. 5 that was cloned out of the hybridoma E2.4.

FIG. 7 is an amino acid sequence of a kappa light chain immunoglobulin molecule that is secreted by the hybridoma E2.4. Differences between the sequence encoded by light chain variable gene 018 and the sequence of the E2.4 secreted light chain are indicated in bold and enlarged font. The contiguous sequence from CDR1 through CDR3 is indicated by underlining and CDR1, CDR2, and CDR3 sequences are each indicated by double underlining.

FIG. 8 is a nucleotide sequence of the cDNA encoding the kappa light chain immunoglobulin molecule of FIG. 7 that was cloned out of the hybridoma E2.4.

FIG. 9 is an amino acid sequence of a heavy chain immunoglobulin molecule that is secreted by the hybridoma E2.5. Differences between the sequence encoded by heavy chain variable gene 4-31 and the sequence of the E2.5 secreted heavy chain are indicated in bold and enlarged font. The contiguous sequence from CDR1 through CDR3 is indicated by underlining and CDR1, CDR2, and CDR3 sequences are each indicated by double underlining.

FIG. 10 is a nucleotide sequence of the cDNA encoding the heavy chain immunoglobulin molecule of FIG. 9 that was cloned out of the hybridoma E2.5.

FIG. 11 is an amino acid sequence of a kappa light chain immunoglobulin molecule that is secreted by the hybridoma E2.5. Differences between the sequence encoded by light chain variable gene 018 and the sequence of the E2.5 secreted light chain are indicated in bold and enlarged font. The contiguous sequence from CDR1 through CDR3 is indicated by underlining and CDR1, CDR2, and CDR3 sequences are each indicated by double underlining.

FIG. 12 is a nucleotide sequence of the cDNA encoding the kappa light chain immunoglobulin molecule of FIG. 11 that was cloned out of the hybridoma E2.5.

FIG. 13 is an amino acid sequence of a heavy chain immunoglobulin molecule that is secreted by the hybridoma E6.2. Differences between the sequence encoded by heavy chain variable gene 4-31 and the sequence of the E6.2 secreted heavy chain are indicated in bold and enlarged font. The contiguous sequence from CDR1 through CDR3 is indicated by underlining and CDR1, CDR2, and CDR3 sequences are each indicated by double underlining.

FIG. 14 is a nucleotide sequence of the cDNA encoding the heavy chain immunoglobulin molecule of FIG. 13 that was cloned out of the hybridoma E6.2.

FIG. 15 is an amino acid sequence of a kappa light chain immunoglobulin molecule that is secreted by the hybridoma E6.2. Differences between the sequence encoded by light chain variable gene 018 and the sequence of the E6.2 secreted light chain are indicated in bold and enlarged font. The contiguous sequence from CDR1 through CDR3 is indicated by underlining and CDR1, CDR2, and CDR3 sequences are each indicated by double underlining.

FIG. 16 is a nucleotide sequence of the cDNA encoding the kappa light chain immunoglobulin molecule of FIG. 15 that was cloned out of the hybridoma E6.2.

FIG. 17 is an amino acid sequence of a heavy chain immunoglobulin molecule that is secreted by the hybridoma E6.4. Differences between the sequence encoded by heavy chain variable gene 4-31 and the sequence of the E6.4 secreted heavy chain are indicated in bold and enlarged font. The contiguous sequence from CDR1 through CDR3 is indicated by underlining and CDR1, CDR2, and CDR3 sequences are each indicated by double underlining.

FIG. 18 is a nucleotide sequence of the cDNA encoding the heavy chain immunoglobulin molecule of FIG. 17 that was cloned out of the hybridoma E6.2.

FIG. 19 is an amino acid sequence of a kappa light chain immunoglobulin molecule that is secreted by the hybridoma E6.4. Differences between the sequence encoded by light chain variable gene 018 and the sequence of the E6.4 secreted light chain are indicated in bold and enlarged font. The contiguous sequence from CDR1 through CDR3 is indicated by underlining and CDR1, CDR2, and CDR3 sequences are each indicated by double underlining.

FIG. 20 is a nucleotide sequence of the cDNA encoding the kappa light chain immunoglobulin molecule of FIG. 19 that was cloned out of the hybridoma E6.4.

FIG. 21 is an amino acid sequence of a heavy chain immunoglobulin molecule that is secreted by the hybridoma E2.11. Differences between the sequence encoded by heavy chain variable gene 4-61 and the sequence of the E2.11 secreted heavy chain are indicated in bold and enlarged font. The contiguous sequence from CDR1 through CDR3 is indicated by underlining and CDR1, CDR2, and CDR3 sequences are each indicated by double underlining.

FIG. 22 is a nucleotide sequence of the cDNA encoding the heavy chain immunoglobulin molecule of FIG. 21 that was cloned out of the hybridoma E2.11.

FIG. 23 is an amino acid sequence of a kappa light chain immunoglobulin molecule that is secreted by the hybridoma E2.11. Differences between the sequence encoded by light chain variable gene 018 and the sequence of the E2.11 secreted light chain are indicated in bold and enlarged font. The contiguous sequence from CDR1 through CDR3 is indicated by underlining and CDR1, CDR2, and CDR3 sequences are each indicated by double underlining.

FIG. 24 is a nucleotide sequence of the cDNA encoding the kappa light chain immunoglobulin molecule of FIG. 23 that was cloned out of the hybridoma E2.11.

FIG. 25 is an amino acid sequence of a heavy chain immunoglobulin molecule that is secreted by the hybridoma E6.3. Differences between the sequence encoded by heavy chain variable gene 4-61 and the sequence of the E6.3 secreted heavy chain are indicated in bold and enlarged font. The contiguous sequence from CDR1 through CDR3 is indicated by underlining and CDR1, CDR2, and CDR3 sequences are each indicated by double underlining.

FIG. 26 is a nucleotide sequence of the cDNA encoding the heavy chain immunoglobulin molecule of FIG. 25 that was cloned out of the hybridoma E6.3.

FIG. 27 is an amino acid sequence of a kappa light chain immunoglobulin molecule that is secreted by the hybridoma E6.3. Differences between the sequence encoded by light chain variable gene 018 and the sequence of the E6.3 secreted light chain are indicated in bold and enlarged font. The contiguous sequence from CDR1 through CDR3 is indicated by underlining and CDR1, CDR2, and CDR3 sequences are each indicated by double underlining.

FIG. 28 is a nucleotide sequence of the cDNA encoding the kappa light chain immunoglobulin molecule of FIG. 27 that was cloned out of the hybridoma E6.3.

FIG. 29 is an amino acid sequence of a heavy chain immunoglobulin molecule that is secreted by the hybridoma E7.6.3. Differences between the sequence encoded by heavy chain variable gene 4-61 and the sequence of the E7.6.3 secreted heavy chain are indicated in bold and enlarged font. The contiguous sequence from CDR1 through CDR3 is indicated by underlining and CDR1, CDR2, and CDR3 sequences are each indicated by double underlining.

FIG. 30 is a nucleotide sequence of the cDNA encoding the heavy chain immunoglobulin molecule of FIG. 29 that was cloned out of the hybridoma E7.6.3.

FIG. 31 is an amino acid sequence of a kappa light chain immunoglobulin molecule that is secreted by the hybridoma E7.6.3. Differences between the sequence encoded by light chain variable gene 018 and the sequence of the E7.6.3 secreted light chain are indicated in bold and enlarged font. The contiguous sequence from CDR1 through CDR3 is indicated by underlining and CDR1, CDR2, and CDR3 sequences are each indicated by double underlining.

FIG. 32 is a nucleotide sequence of the cDNA encoding the kappa light chain immunoglobulin molecule of FIG. 31 that was cloned out of the hybridoma E7.6.3.

FIG. 33 provides a comparison of specific anti-EGF-r antibody heavy chain amino acid sequence comparisons with the amino acid sequence of the particular $V_H$ gene which encodes the heavy chain of the particular antibody.

FIG. 34 provides a comparison of specific anti-EGF-r antibody light chain amino acid sequence comparisons with the amino acid sequence of the particular Vκ gene which encodes the light chain of the particular antibody.

FIG. 35 shows blockage EGF binding to human epidermoid carcinoma A431 cells by human anti-EGF-r antibodies in vitro, where (□) depicts the results achieved by an anti-EGF-r antibody in accordance with the invention, (●) depicts the results achieved by the murine monoclonal antibody 225, and (▲) depicts the results achieved by a control, nonspecific, human IgG2 antibody.

FIG. 36 shows inhibition of EGF binding to human epidermoid carcinoma A431 cells by human anti-EGF-r antibodies in vitro, where (□) depicts the results achieved by the murine monoclonal antibody 225, (○) depicts the results achieved by the murine monoclonal antibody 528, (▼) depicts the results achieved using the E1.1 antibody in accordance with the invention, (▲) depicts the results achieved using the E2.4 antibody in accordance with the invention, (▶) depicts the results achieved using the E2.5 antibody in accordance with the invention, (◀) depicts the results achieved using the E2.6 antibody in accordance with the invention, (♦) depicts the results achieved using the E2.11 antibody in accordance with the invention, and (✪) depicts the results achieved using a control, nonspecific human IgG2 antibody.

FIG. 37 shows inhibition of TGF-αbinding to human epidermoid carcinoma A431 cells by human anti-EGF-r antibodies in vitro, where (□) depicts the results achieved by the murine monoclonal antibody 225, (♦) depicts the results achieved using the E6.2 antibody in accordance with the invention, (●) depicts the results achieved using the E6.3 antibody in accordance with the invention, (▲) depicts the results achieved using the E7.2 antibody in accordance with the invention, (■) depicts the results achieved using the E7.10 antibody in accordance with the invention, (▼) depicts the results achieved using the E7.6.3, and (✪) depicts the results achieved using a control, nonspecific human IgG2 antibody.

Figure 40:
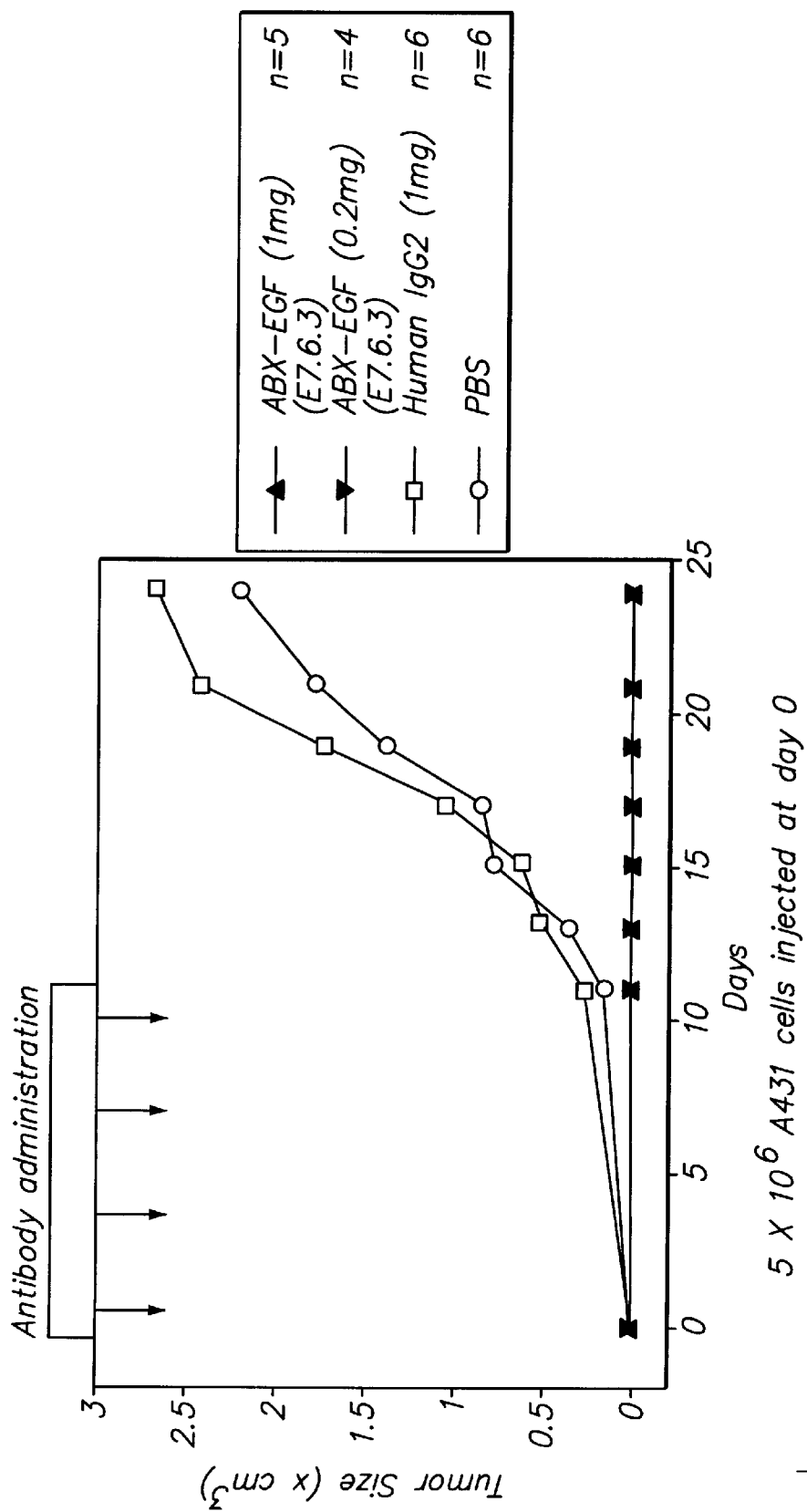

FIG. 40 shows the inhibition of human epidermoid carcinoma A431 cell growth in nude mice through use of human anti-EGF-r antibodies in accordance with the invention in vivo. In the Figure, (▲) depicts the results achieved with a dosage of 1 mg of a human anti-EGF-r antibody in accordance with the present invention, (▼) depicts the results achieved with a dosage of 0.2 mg of a human anti-EGF-r antibody in accordance with the present invention, (□) depicts the results achieved by a control, nonspecific, human IgG2 antibody, and (○) depicts the results achieved utilizing phosphate buffered saline as a control.

FIG. 41 shows data related to the inhibition of epidermoid carcinoma formation in nude mice through use of human anti-EGF-r antibodies in accordance with the invention in vivo showing tumor incidence at day 19.

Figure 42:
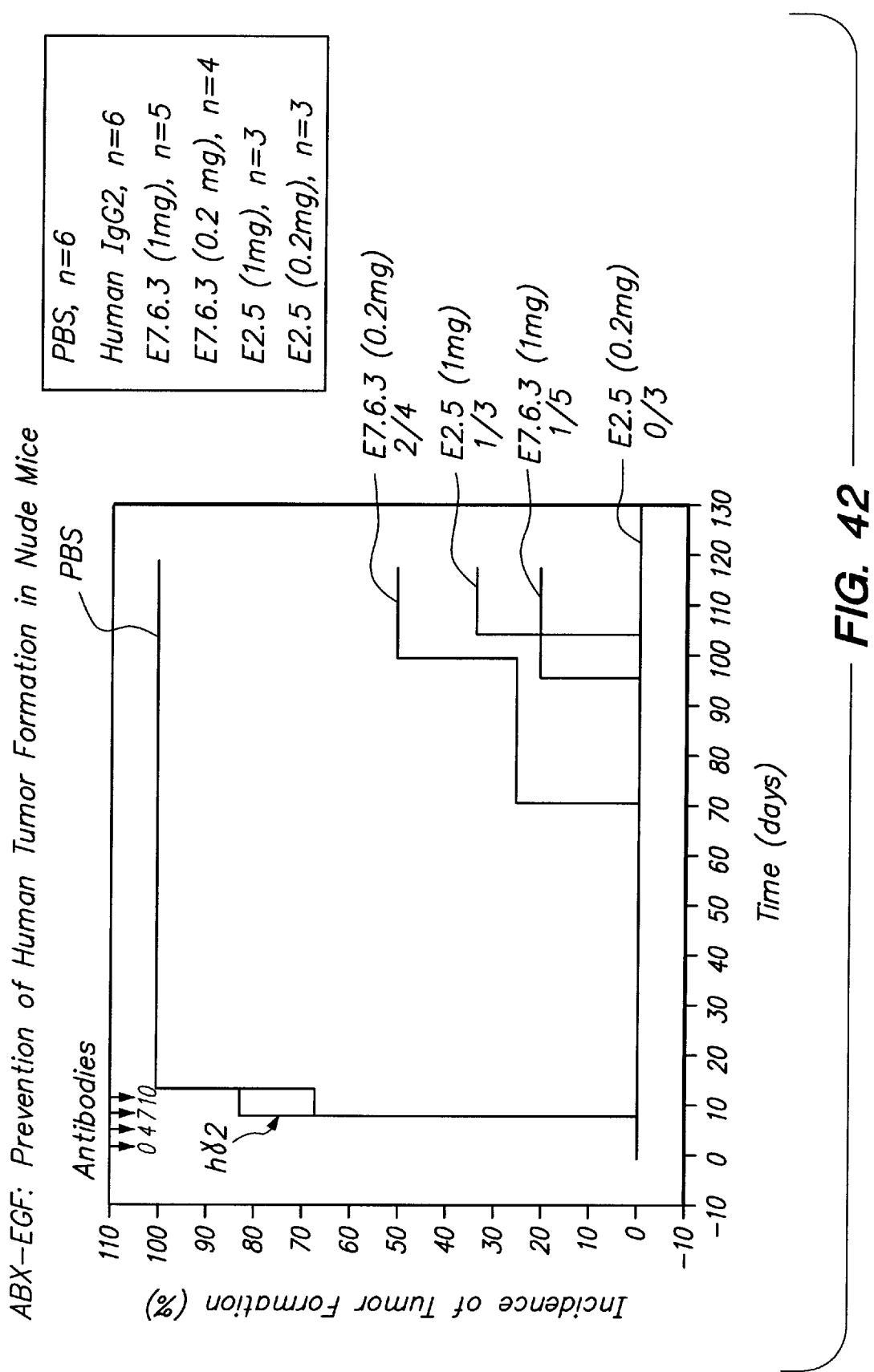

FIG. 42 shows data related to the inhibition of epidermoid carcinoma formation in nude mice through use of human anti-EGF-r antibodies in accordance with the invention in vivo showing tumor incidence at day 120.

Figure 43:
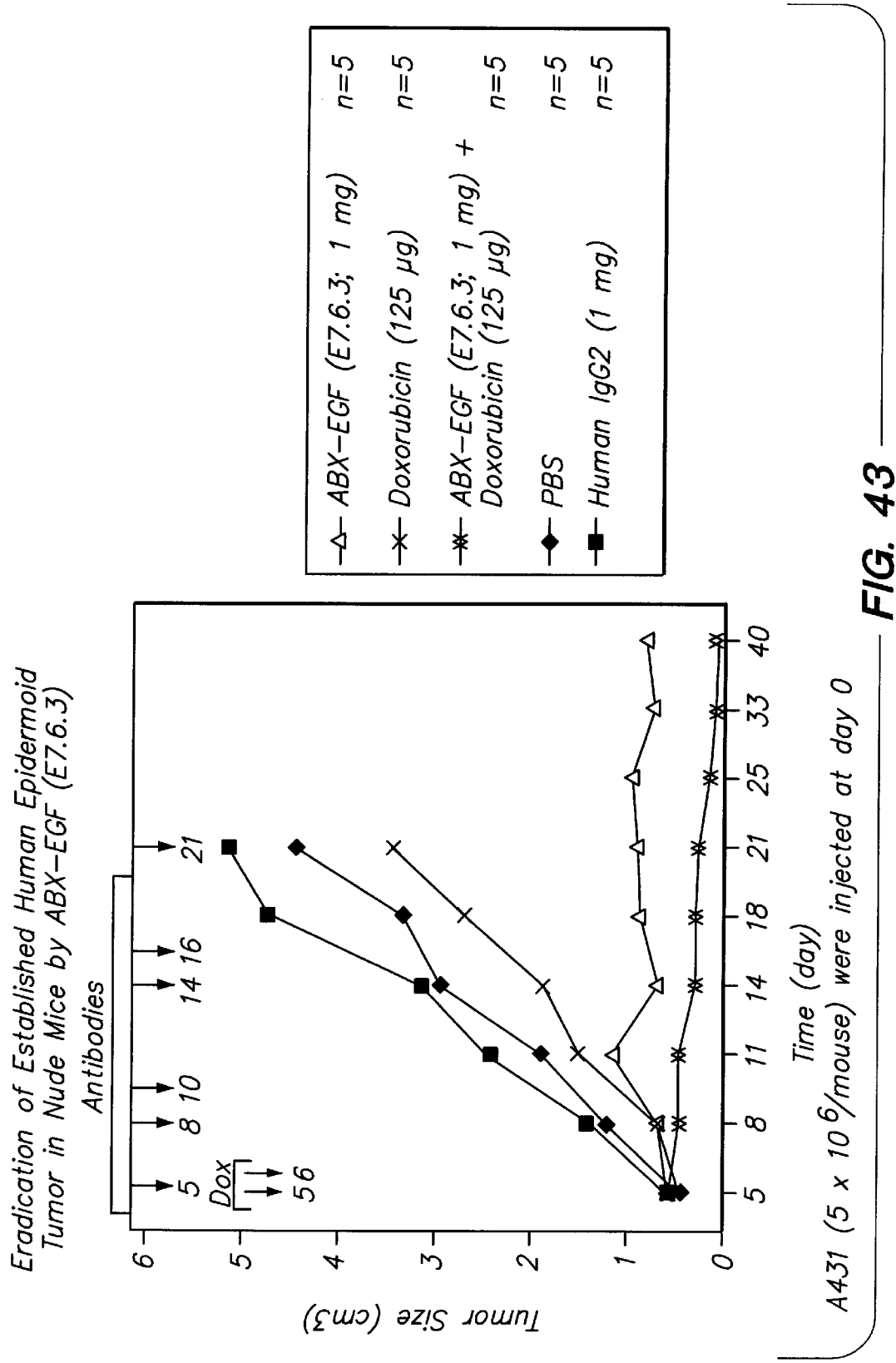

FIG. 43 shows data related to the eradication of an established human epidermoid tumor in nude mice through use of human anti-EGF-r antibodies in accordance with the invention in vivo. In the Figure, (▲) depicts the results achieved with multiple doses of 1 mg each of a human anti-EGF-r antibody in accordance with the present invention (E7.6.3), (X) depicts the results achieved with two doses of 125 μg each of doxorubicin, (*) depicts the results achieved with a multiple doses of 1 mg each of a human anti-EGF-r antibody in accordance with the present invention (E7.6.3) in combination with two doses of 125 μg each of doxorubicin, (■) depicts the results achieved by a control, nonspecific, human IgG2 antibody, and (♦) depicts the results achieved utilizing phosphate buffered saline as a control.

Figure 44:
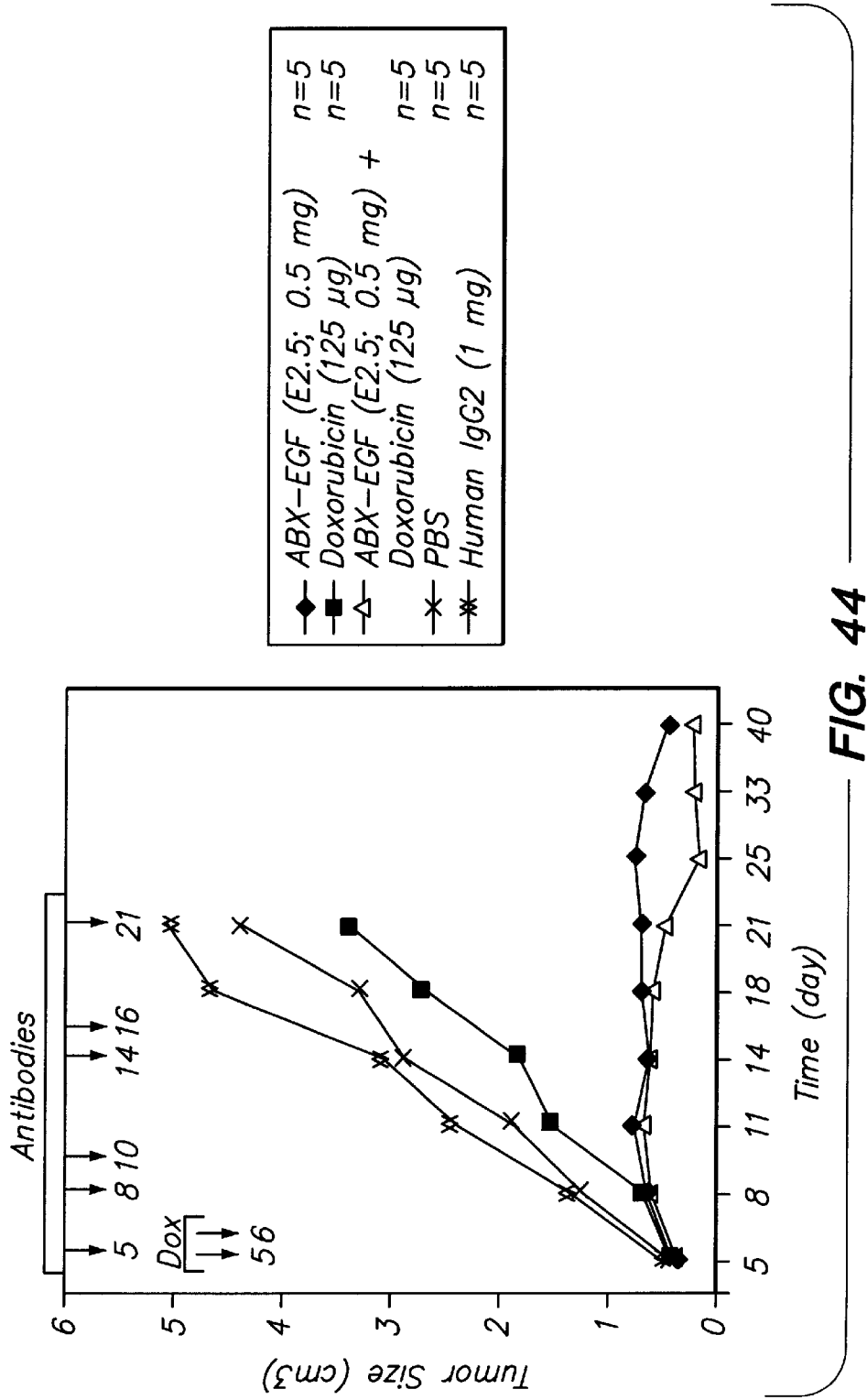

FIG. 44 shows data related to the eradication of an established human epidermoid tumor in nude mice through use of human anti-EGF-r antibodies in accordance with the invention in vivo. In the Figure, (♦) depicts the results achieved with multiple doses of 0.5 mg each of a human anti-EGF-r antibody in accordance with the present invention (E2.5), (■) depicts the results achieved with two doses of 125 μg each of doxorubicin, (▲) depicts the results achieved with multiple doses of 0.5 mg each of a human anti-EGF-r antibody in accordance with the present invention (E2.5) in combination with two doses of 125 μg each of doxorubicin, (X) depicts the results achieved utilizing phosphate buffered saline as a control, and (*) depicts the results achieved utilizing a control, nonspecific, human IgG2 antibody at a dose of 1 mg.

SUMMARY OF THE INVENTION

In accordance with a first aspect of the present invention, there is provided an antibody against epidermal growth factor receptor comprising a heavy chain variable region amino acid sequence wherein a portion of the sequence is encoded by a human $V_H$ 4 family gene and any of the mutations thereto represented by the nucleotide sequences shown in FIGS. 2, 6, 10, 14, 18, 22, 26, and 30. In a preferred embodiment, the heavy chain variable region amino acid sequence comprises an Aspartic Acid amino acid substitution at residue 10.

In accordance with a second aspect of the present invention, there is provided an antibody against epidermal growth factor receptor comprising a heavy chain variable region amino acid sequence wherein a portion of the sequence is encoded by a human $V_H$ 4-31 gene and any of the mutations thereto represented by the nucleotide sequences shown in FIGS. 2, 6, 10, 14, and 18. In a preferred embodiment, the heavy chain variable region comprises the contiguous sequence from CDR1 through CDR3 as represented in SEQ ID NO:23. In a preferred embodiment, the antibody further comprises a light chain variable region comprising the sequence represented by SEQ ID NO:24. In a preferred embodiment, the heavy chain variable region comprises the contiguous sequence from CDR1 through CDR3 as represented in SEQ ID NO:25. In a preferred embodiment, the antibody further comprises a light chain variable region comprising the sequence represented by SEQ ID NO:26. In a preferred embodiment, the heavy chain variable region comprises the contiguous sequence from CDR1 through CDR3 as represented in SEQ ID NO:27. In a preferred embodiment, the antibody further comprises a light chain variable region comprising the sequence represented by SEQ ID NO:28. In a preferred embodiment, the heavy chain variable region comprises the contiguous sequence from CDR1 through CDR3 as represented in SEQ ID NO:29. In a preferred embodiment, the antibody further comprises a light chain variable region comprising the sequence represented by SEQ ID NO:30. In a preferred embodiment, the heavy chain variable region comprises the contiguous sequence from CDR1 through CDR3 as represented in SEQ ID NO:31. In a preferred embodiment, the antibody further comprises a light chain variable region comprising the sequence represented by SEQ ID NO:32.

In accordance with the third aspect of the present invention, there is provided an antibody against epidermal growth factor receptor comprising a heavy chain variable region amino acid sequence wherein a portion of the sequence is encoded by a human $V_H$ 4-61 gene and any of the mutations thereto represented by the nucleotide sequences shown in FIGS. 22, 26, and 30. In a preferred embodiment, the heavy chain variable region comprises the contiguous sequence from CDR1 through CDR3 as represented in SEQ ID NO:33. In a preferred embodiment, the antibody further comprises a light chain variable region comprising the sequence represented by SEQ ID NO:34. In a preferred embodiment, the heavy chain variable region comprises the contiguous sequence from CDR1 through CDR3 as represented in SEQ ID NO:35. In a preferred embodiment, the antibody further comprises a light chain variable region comprising the sequence represented by SEQ ID NO:36. In a preferred embodiment, the heavy chain variable region comprises the contiguous sequence from CDR1 through CDR3 as represented in SEQ ID NO:37. In a preferred embodiment, the antibody further comprises a light chain variable region comprising the sequence represented by SEQ ID NO:38.

In accordance with a fourth aspect of the present invention, there is provided an antibody against epidermal growth factor receptor comprising a light chain variable region amino acid sequence wherein a portion of the sequence is encoded by a human Vκ I family gene and any of the mutations thereto represented by the nucleotide sequences shown in FIGS. 4, 8, 12, 16, 20, 24, 28, and 32. In a preferred embodiment, the light chain variable region comprises the sequence represented by SEQ ID NO:24. In a preferred embodiment, the light chain variable region comprises the sequence represented by SEQ ID NO:26. In a preferred embodiment, the light chain variable region comprises the sequence represented by SEQ ID NO:28. In a preferred embodiment, the light chain variable region comprises the sequence represented by SEQ ID NO:30. In a preferred embodiment, the light chain variable region comprises the sequence represented by SEQ ID NO:32. In a preferred embodiment, the light chain variable region comprises the sequence represented by SEQ ID NO:34. In a preferred embodiment, the light chain variable region comprises the sequence represented by SEQ ID NO:36. In a preferred embodiment, the light chain variable region comprises the sequence represented by SEQ ID NO:38.

In accordance with a fifth aspect of the present invention, there is provided an antibody against epidermal growth factor receptor comprising a heavy chain variable region comprising a contiguous sequence from CDR1 through CDR3 as represented in SEQ ID NO:23. In a preferred embodiment, the antibody further comprises a light chain variable region comprising the sequence represented by SEQ ID NO:24.

In accordance with a sixth aspect of the present invention, there is provided an antibody against epidermal growth factor receptor comprising a heavy chain variable region comprising a contiguous sequence from CDR1 through CDR3 as represented in SEQ ID NO:25. In a preferred embodiment, the antibody further comprises a light chain variable region comprising the sequence represented by SEQ ID NO:26.

In accordance with a seventh aspect of the present invention, there is provided an antibody against epidermal growth factor receptor comprising a heavy chain variable region comprises a contiguous sequence from CDR1 through CDR3 as represented in SEQ ID NO:27. In a preferred embodiment, the antibody further comprises a light chain variable region comprising the sequence represented by SEQ ID NO:28.

In accordance with a eighth aspect of the present invention, there is provided an antibody against epidermal growth factor receptor comprising a heavy chain variable region comprising a contiguous sequence from CDR1 through CDR3 as represented in SEQ ID NO:29. In a preferred embodiment, the antibody further comprises a light chain variable region comprising the sequence represented by SEQ ID NO:30.

In accordance with a ninth aspect of the present invention, there is provided an antibody against epidermal growth factor receptor comprising a heavy chain variable region comprising a contiguous sequence from CDR1 through CDR3 as represented in SEQ ID NO:31. In a preferred embodiment, the antibody further comprises a light chain variable region comprising the sequence represented by SEQ ID NO:32.

In accordance with a tenth aspect of the present invention, there is provided an antibody against epidermal growth factor receptor comprising a heavy chain variable region comprising a contiguous sequence from CDR1 through CDR3 as represented in SEQ ID NO:33. In a preferred embodiment, the antibody further comprises a light chain variable region comprising the sequence represented by SEQ ID NO:34.

In accordance with an eleventh aspect of the present invention, there is provided an antibody against epidermal growth factor receptor comprising a heavy chain variable region comprising a contiguous sequence from CDR1 through CDR3 as represented in SEQ ID NO:35. In a preferred embodiment, the antibody further comprises a light chain variable region comprising the sequence represented by SEQ ID NO:27.

In accordance with a twelfth aspect of the present invention, there is provided an antibody against epidermal growth factor receptor comprising a heavy chain variable region comprising a contiguous sequence from CDR1 through CDR3 as represented in SEQ ID NO:37. In a preferred embodiment, the antibody further comprises a light chain variable region comprising the sequence represented by SEQ ID NO:38.

In accordance with a thirteenth aspect of the present invention, there is provided, in a method for treating a solid tumor with an antibody against epidermal growth factor receptor, the improvement comprising administering to a patient having a solid tumor one of the foregoing antibodies of the invention.

DETAILED DESCRIPTION OF THE PREFERRED EMBODIMENTS

In accordance with the present invention, there are provided fully human monoclonal antibodies against human epidermal growth factor receptor (EGF-r). Nucleotide sequences encoding and amino acid sequences comprising heavy and light chain immunoglobulin molecules, particularly sequences corresponding to a contiguous heavy and light chain sequences from CDR1 through CDR3, are provided. Hybridomas expressing such immunoglobulin molecules and monoclonal antibodies are also provided.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules represented by FIGS. 1, 5, 9, 13, 17, 21, 25, and 29 and the human kappa light chain immunoglobulin molecules represented by FIGS. 3, 7, 11, 15, 19, 23, 27, and 31, as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87–108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101–110 (Volume 5, National Biomedical Research Foundation (1972)) and Supplement 2 to this volume, pp. 1–10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24–48 nucleotide (8–16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2$^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physiocochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a EGF-r, under suitable binding conditions, (2) ability to EGF binding to its receptor, or (3) ability to inhibit EGF-r expressing cell growth in vitro or in vivo. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drus with properties analogous to those of the template peptide. These types of non-peptide compound are termed "peptide mimetics" or "peptidomimetics". Fauchere, *J. Adv. Drug Res.* 15:29 (1986); Veber and Freidinger TINS p.392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ $\mu$M, preferably $\leq 100$ nM and most preferably $\leq 10$ nM.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, $\beta$-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibody Structure

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about I100 to 1 10 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901–917 (1987); Chothia et al. *Nature* 342:878–883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315–321 (1990), Kostelny et al. *J. Immunol.* 148:1547–1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Preparation of Antibodies

Antibodies in accordance with the invention are preferably prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the Background, herein. In particular, however, a preferred embodiment of transgenic production of mice and antibodies therefrom is disclosed in U.S. patent application Ser. No. 08/759,620, filed Dec. 3, 1996, the disclosure of which is hereby incorporated by reference. See also Mendez et al. *Nature Genetics* 15:146–156 (1997), the disclosure of which is hereby incorporated by reference.

Through use of such technology, we have produced fully human monoclonal antibodies to a variety of antigens. Essentially, we immunize XenoMouse™ lines of mice with an antigen of interest, recover lymphatic cells (such as B-cells) from the mice that express antibodies, fuse such recovered cells with a myeloid-type cell line to prepare immortal hybridoma cell lines, and such hybridoma cell lines are screened and selected to identify hybridoma cell lines that produce antibodies specific to the antigen of interest. We utilized these techniques in accordance with the present invention for the preparation of antibodies specific to EGF-r. Herein, we describe the production of eight hybridoma cell lines that produce antibodies specific to EGF-r. Further, we provide a characterization of the antibodies produced by such cell lines, including nucleotide and amino acid sequence analyses of the heavy and light chains of such antibodies.

The hybridoma cell lines discussed herein are designated E1.1, E2.4, E2.5, E6.2, E6.4, E2.11, E6.3, and E7.6.3. Each of the antibodies produced by the aforementioned cell lines are fully human IgG2 heavy chains with human kappa light chains. In general, antibodies in accordance with the invention possess very high affinities, typically possessing Kd's of from about $10^{-9}$ through about $10^{-11}$ M, when measured by either solid phase and solution phase.

As will be appreciated, antibodies in accordance with the present invention can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912, 040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide (s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive EGF-r binding properties.

Figure 38:
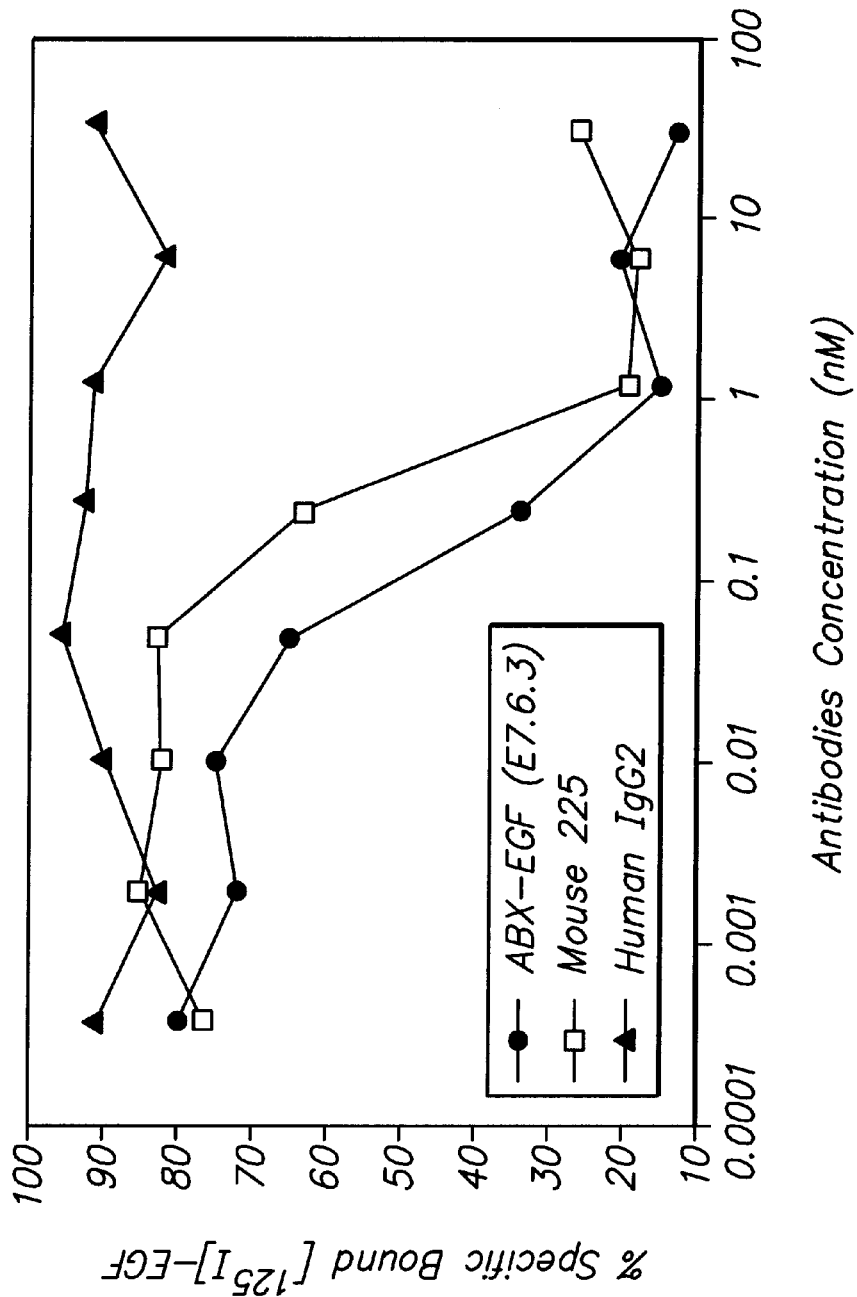
FIG. 38 shows inhibition of EGF binding to human colon carcinoma SW948 cells by human anti-EGF-r antibodies in vitro, where (●) depicts the results achieved by an anti-EGF-r antibody in accordance with the invention, (□) depicts the results achieved by the murine monoclonal antibody 225, and (▲) depicts the results achieved by a control, nonspecific, human IgG2 antibody.
Figure 39:
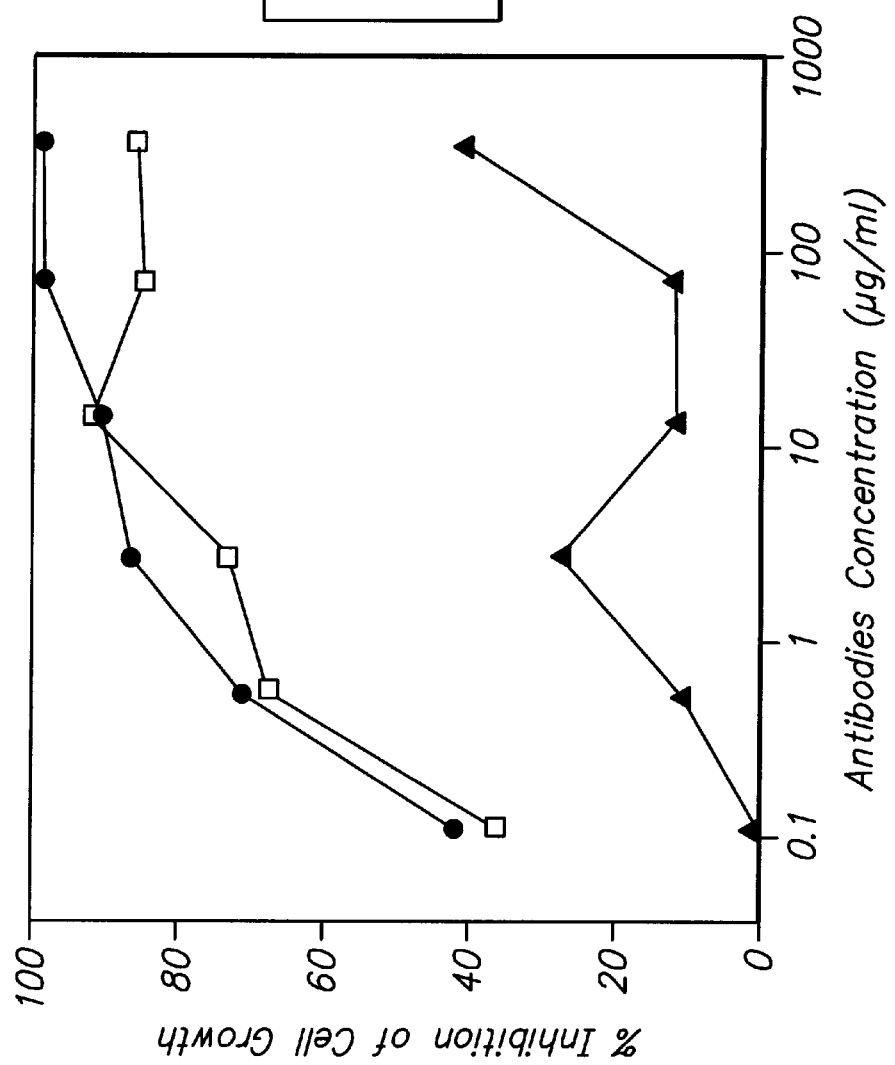
FIG. 39 shows that human anti-EGF-r antibodies derived from XenoMouse II strains inhibit growth of SW948 cells in vitro, where (○) depicts the results achieved by an anti-EGF-r antibody in accordance with the invention, (□) depicts the results achieved by the murine monoclonal antibody 225, and (▲) depicts the results achieved by a control, nonspecific, human IgG2 antibody.

Antibodies in accordance with the present invention are potent inhibitors of EGF and TGF-α binding to its receptor, EGF-r. Such results are discussed in Examples 5 and 6 and shown in FIGS. 35 through 38. Consistent with such results, and as shown in FIG. 39 and discussed in connection with Example 7, antibodies in accordance with the present invention also inhibit the growth of certain human carcinoma cell lines in vitro. Antibodies in accordance with the present invention also prevent the growth of certain human carcinomas in vivo. Such results are shown in FIGS. 40 through 42 and discussed in connection with Example 8. In Example 9, we demonstrate that antibodies in accordance with the present invention, at least in combination with an antineoplastic agent, will eradicate an existing tumor in an animal. Moreover, antibody therapy, as a monotherapy (i.e., not in combination with an antineoplastic agent) appears possible in accordance with the antibodies in accordance with the present invention, where it did not appear possible in the prior art, for example through the use of the antibody 225. Such results are discussed in connection with Example 9 and shown in FIGS. 43–44.

The results demonstrated in accordance with the present invention indicate that antibodies in accordance with the present invention possess certain qualities that may make the present antibodies more efficacious than current therapeutic antibodies against EGF-r, e.g., 225. The 225 antibody in clinical development by Imclone is a chimeric IgG1 antibody with an affinity of $2 \times 10^{-10}$ M, which, while appearing efficacious in combination therapy with an antineoplastic agent, does not appear very efficacious in monotherapy. In contrast, antibodies in accordance with the invention (and particularly the E2.5 and E7.6.3 antibodies of the invention) have significantly higher affinities (E2.5:$1.6 \times 10^{-11}$ M; E7.6.3:$5.7 \times 10^{-11}$ M) and appear efficacious in monotherapy in addition to combination therapy with an antineoplastic agent and at lower doses than with the C225 antibody.

EXAMPLES

The following examples, including the experiments conducted and results achieved are provided for illustrative purposes only and are not to be construed as limiting upon the present invention.

Example 1

Generation of Anti-EGF-r-Antibody Producing Hybridomas

Antibodies of the invention were prepared, selected, and assayed in accordance with the present Example.

Immunization and hybridoma generation: XenoMice (8 to 10 weeks old) were immunized intraperitoneally with $2 \times 10^7$ A431 (ATCC CRL-7907) cells resuspended in phosphate buffered saline (PBS). This dose was repeated three times. Four days before fusion, the mice received a final injection of cells in PBS. Spleen and lymph node lymphocytes from immunized mice were fused with the non-secretory myeloma NSO-bc12 line (Ray and Diamond, 1994) and were subjected to HAT selection as previously described (Galfre and Milstein, 1981). A large panel of hybridomas all secreting EGF-r specific human $IgG_2\kappa$ (as detected below) antibodies were recovered. As described in Example 2, certain of the antibodies selected from the panel were selected for their ability to compete with the 225 antibody.

ELISA assay: ELISA for determination of antigen-specific antibodies in mouse serum and in hybridoma supernatants was carried out as described (Coligan et al., 1994) using affinity-purified EGF-r from A431 cells (Sigma, E-3641) to capture the antibodies. The concentrations of human and mouse immunoglobulins were determined using the following capture antibodies: rabbit anti-human IgG (Southern Biotechnology, 6145-01), goat anti-human Igκ (Vector Laboratories, AI-3060), mouse anti-human IgM (CGI/ATCC, HB-57), for human gamma, kappa, and mu Ig, respectively, and goat anti-mouse IgG (Caltag, M 30100), goat anti-mouse Igκ (Southern Biotechnology, 1050-01), goat anti-mouse IgM (Southern Biotechnology, 1020-01), and goat anti-mouse λ (Southern Biotechnology, 1060-01) to capture mouse gamma, kappa, mu, and lambda Ig, respectively. The detection antibodies used in ELISA experiments were goat anti-mouse IgG-HRP (Caltag, M-30107), goat anti-mouse Igκ-HRP (Caltag, M 33007), mouse anti-human IgG2-HRP (Southern Biotechnology, 9070-05), mouse anti-human IgM-HRP (Southern Biotechnology, 9020-05), and goat anti-human kappa-biotin (Vector, BA-3060). Standards used for quantitation of human and mouse Ig were: human $IgG_2\kappa$ (Calbiochem, 400122), human IgMκ (Cappel, 13000), mouse IgGκ (Cappel 55939), mouse IgMκ (Sigma, M-3795), and mouse-$IgG_3\lambda$ (Sigma, M-9019).

Determination of affinity constants of fully human Mabs by BIAcore: Affinity measurement of purified human monoclonal antibodies, Fab fragments, or hybridoma supernatants by plasmon resonance was carried out using the BIAcore 2000 instrument, using general procedures outlined by the manufacturers.

Kinetic analysis of the antibodies was carried out using antigens immobilized onto the sensor surface at a low density. Soluble EGF-r purified from A431 cell membranes (Sigma, E-3641) was generally used at a surface density of 228 RU. The dissociation (kd) and association (ka) rates were determined using the software provided by the manufacturer (BIA evaluation 2.1).

Determination of affinity constants in solution by ELISA: In order to determine antibody binding affinity in solution by ELISA, various concentrations of the monoclonal nil antibodies to EGF-r were incubated with EGF-r at a constant concentration until equilibrium was reached. Thereafter, the concentration of the free EGF-r in the reaction solution was determined by an indirect ELISA. Accordingly, the monoclonal antibodies at concentrations of between $3.0 \times 10^{-11}$ M through $2.7 \times 10^{-7}$ M were incubated with EGF-r at a concentration of $4 \times 10^{-10}$ M in 200 μl of PBS with 0.5% BSA for 15 hrs at room temperature. After incubation, 70 μl of each mixture was transferred into the wells of 96-well microtiter plates previously coated with the same monoclonal antibody (100 μl/well, at 2 μg/ml in coating buffer) and incubated for 15 min at room temperature. After washing with washing buffer, the EGF-r retained on the plate was detected by mouse anti-EGF-r-HRP, which binds to the carbohydrate of the EGF-r protein. The concentration of EGF-r was calculated against its standard and used for the calculation of bound and free antibodies in the original antigen-antibody reaction solution. The binding affinity of each monoclonal antibody to EGF-r was calculated using Scatchard analysis.

Receptor binding assays: The EGF receptor binding assay was carried out with A431 cells or SW948 cells ($0.4 \times 10^6$ cells per well) which were incubated with varying concentrations of antibodies in PBS binding buffer for 30 minutes at 4° C. 0.1 nM [$^{125}$I]EGF (Amersham, IM-196) or [$^{125}$I] TGF-α (Amersham) was added to each well, and the plates were incubated for 90 min at 4° C. The plates were washed five times, air-dried and counted in a scintillation counter. Anti-EGF-r mouse antibodies 225 and 528 (Calbiochem) were used as controls.

Example 2

Co-Selection of Anti-EGF-r-Antibodies with the m225 Antibody

As discussed above, the antibody 225 has been demonstrated to possess a high affinity for, and effective inhibition of the binding of EGF and TGF-α to EGF-r. Thus, we expected that if we selected human antibodies against EGF-r that are prepared in accordance with the present invention with the antibody 225 in a competition assay, antibodies to the same or similar epitope to which the 225 antibody binds would be selected.

Accordingly, we conducted BIAcore assays in which soluble EGF-r purified from A431 cell membranes (Sigma, E-3641) was pretreated with the antibody 225 and thereafter treated with antibodies of the invention. Where antibodies of the invention did not bind, such antibodies of the invention were screened for binding affinity as described above.

In the following Table, affinity measurements for certain of the antibodies selected in this manner are provided:

TABLE I

| Hybri-doma | $k_{on}$ ($M^{-1}S^{-1}$) | $K_{off}$ ($S^{-1}$) | $K_D$ (M) | Solid Phase (by BIAcore) Surface Density [RU] | In Solution By ELISA KD (M) |
|---|---|---|---|---|---|
| E1.1 | $2.3 \times 10^6$ | $1.7 \times 10^{-4}$ | $7.6 \times 10^{-11}$ | 228 | $1.1 \times 10^{-10}$ |
| E2.4 | $2.8 \times 10^6$ | $9.78 \times 10^{-5}$ | $3.5 \times 10^{-11}$ | 818 | $1.1 \times 10^{-10}$ |
| E2.5 | $1.2 \times 10^6$ | $1.9 \times 10^{-5}$ | $1.6 \times 10^{-11}$ | 228 | $3.6 \times 10^{-10}$ |
| E2.11 | $1.9 \times 10^6$ | $3.0 \times 10^{-4}$ | $1.6 \times 10^{-10}$ | 228 | $1.1 \times 10^{-10}$ |
| E7.6.3 | $2.0 \times 10^6$ | $1.1 \times 10^{-4}$ | $5.7 \times 10^{-11}$ | 228 | ND |

As will be observed, antibodies selected in this manner possess exceptionally high affinities and binding constants.

Example 3

Structures of Anti-EGF-r-Antibodies Prepared in Accordance with the Invention

In the following discussion, structural information related to antibodies prepared in accordance with the invention is provided.

In order to analyze structures of antibodies produced in accordance with the invention, we cloned genes encoding the heavy and light chain fragments out of the particular hybridoma. Gene cloning and sequencing was accomplished as follows:

Poly(A)+ mRNA was isolated from approximately 2×10^5 hybridoma cells derived from immunized XenoMice using a Fast-Track kit (Invitrogen). The generation of random primed cDNA was followed by PCR. Human $V_H$ or human $V_K$ family specific variable region primers (Marks et. al., 1991) or a universal human $V_H$ primer, MG-30 (CAGGTGCAGCTGGAGCAGTCIGG) (SEQ ID NO:1) was used in conjunction with primers specific for the human Cγ2 constant region (MG-40d; 5'-GCTGAGGGAGTAGAGTCCTGAGGA-3') (SEQ ID NO:2) or Cκ constant region (hκP2; as previously described in Green et al., 1994). Sequences of human Mabs-derived heavy and kappa chain transcripts from hybridomas were obtained by direct sequencing of PCR products generated from poly(A+) RNA using the primers described above. PCR products were also cloned into pCRII using a TA cloning kit (Invitrogen) and both strands were sequenced using Prism dye-terminator sequencing kits and an ABI 377 sequencing machine. All sequences were analyzed by alignments to the "V BASE sequence directory" (Tomlinson et al., MRC Centre for Protein Engineering, Cambridge, UK) using MacVector and Geneworks software programs.

Hybridoma E1.1

The antibody secreted by the hybridoma E1.1 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E1.1 evidenced the following gene utilization:

$V_H$—4-31
D—2
$J_H$—5
Vκ—018
Jκ—4

As reported in the V BASE sequence directory, the amino acid sequence encoded by the $V_H$ 4-31 gene was determined to be:

VSGGSISSGGYYWSWIRQHPGKGLEWI-GYIYYSGSTYYNPSLKSRVTISVDTSKN-QFSLKLSSVTAADTAVYYCAR (SEQ ID NO:19)

As reported in the V BASE sequence directory, the amino acid sequence encoded by the Vκ (018) gene was determined to be:

TITCQASQDISNYLNWYQQKPGKAP-KLLIYDASNLETGVPSRFSGSGSGTDFT-FTISSLQPEDIATYYCQQYDNLP (SEQ ID NO:20)

Amino acid and nucleotide sequence information respecting the heavy and light chains are provided below in connection with FIGS. 1–4. FIG. 1 is an amino acid sequence of a heavy chain immunoglobulin molecule that is secreted by the hybridoma E1.1. Differences between the sequence encoded by heavy chain variable gene 4-31 and the sequence of the E1.1 secreted heavy chain are indicated in bold and enlarged font. The contiguous sequence from CDR1 through CDR3 is indicated by underlining and CDR1, CDR2, and CDR3 sequences are each indicated by double underlining.

FIG. 2 is a nucleotide sequence of the cDNA encoding the heavy chain immunoglobulin molecule of FIG. 1 that was cloned out of the hybridoma E1.1.

FIG. 3 is an amino acid sequence of a kappa light chain immunoglobulin molecule that is secreted by the hybridoma E1.1. Differences between the sequence encoded by light chain variable gene 018 and the sequence of the E1.1 secreted light chain are indicated in bold and enlarged font. The contiguous sequence from CDR1 through CDR3 is indicated by underlining and CDR1, CDR2, and CDR3 sequences are each indicated by double underlining.

FIG. 4 is a nucleotide sequence of the cDNA encoding the kappa light chain immunoglobulin molecule of FIG. 3 that was cloned out of the hybridoma E1.1.

Hybridoma E2.4

The antibody secreted by the hybridoma E2.4 comprises a human IgG2 antibody having a human kappa light chain.

The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E2.4 evidenced the following gene utilization:

$V_H$—4-31

D—A1/A4

$J_H$—3

Vκ—018

Jκ—4

Amino acid and nucleotide sequence information respecting the heavy and light chains are provided below in connection with FIGS. 5–8. FIG. 5 is an amino acid sequence of a heavy chain immunoglobulin molecule that is secreted by the hybridoma E2.4. Differences between the sequence encoded by heavy chain variable gene 4-31 and the sequence of the E2.4 secreted heavy chain are indicated in bold and enlarged font. The contiguous sequence from CDR1 through CDR3 is indicated by underlining and CDR1, CDR2, and CDR3 sequences are each indicated by double underlining.

FIG. 6 is a nucleotide sequence of the cDNA encoding the heavy chain immunoglobulin molecule of FIG. 5 that was cloned out of the hybridoma E2.4.

FIG. 7 is an amino acid sequence of a kappa light chain immunoglobulin molecule that is secreted by the hybridoma E2.4. Differences between the sequence encoded by light chain variable gene 018 and the sequence of the E2.4 secreted light chain are indicated in bold and enlarged font. The contiguous sequence from CDR1 through CDR3 is indicated by underlining and CDR1, CDR2, and CDR3 sequences are each indicated by double underlining.

FIG. 8 is a nucleotide sequence of the cDNA encoding the kappa light chain immunoglobulin molecule of FIG. 7 that was cloned out of the hybridoma E2.4.

Hybridoma E2.5

The antibody secreted by the hybridoma E2.5 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E2.5 evidenced the following gene utilization:

$V_H$—4-31

D—XP1/21-10

$J_H$—4

Vκ—018

Jκ—2

Amino acid and nucleotide sequence information respecting the heavy and light chains are provided below in connection with FIGS. 9–12. FIG. 9 is an amino acid sequence of a heavy chain immunoglobulin molecule that is secreted by the hybridoma E2.5. Differences between the sequence encoded by heavy chain variable gene 4-31 and the sequence of the E2.5 secreted heavy chain are indicated in bold and enlarged font. The contiguous sequence from CDR1 through CDR3 is indicated by underlining and CDR1, CDR2, and CDR3 sequences are each indicated by double underlining.

FIG. 10 is a nucleotide sequence of the cDNA encoding the heavy chain immunoglobulin molecule of FIG. 9 that was cloned out of the hybridoma E2.5.

FIG. 11 is an amino acid sequence of a kappa light chain immunoglobulin molecule that is secreted by the hybridoma E2.5. Differences between the sequence encoded by light chain variable gene 018 and the sequence of the E2.5 secreted light chain are indicated in bold and enlarged font. The contiguous sequence from CDR1 through CDR3 is indicated by underlining and CDR1, CDR2, and CDR3 sequences are each indicated by double underlining.

FIG. 12 is a nucleotide sequence of the cDNA encoding the kappa light chain immunoglobulin molecule of FIG. 11 that was cloned out of the hybridoma E2.5.

Hybridoma E6.2

The antibody secreted by the hybridoma E6.2 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E6.2 evidenced the following gene utilization:

$V_H$—4-31

D—? (CNTCCCT) (SEQ ID NO:39)

$J_H$—6

Vκ—018

Jκ—1

Amino acid and nucleotide sequence information respecting the heavy and light chains are provided below in connection with FIGS. 13–16. FIG. 13 is an amino acid sequence of a heavy chain immunoglobulin molecule that is secreted by the hybridoma E6.2. Differences between the sequence encoded by heavy chain variable gene 4-31 and the sequence of the E6.2 secreted heavy chain are indicated in bold and enlarged font. The contiguous sequence from CDR1 through CDR3 is indicated by underlining and CDR1, CDR2, and CDR3 sequences are each indicated by double underlining.

FIG. 14 is a nucleotide sequence of the cDNA encoding the heavy chain immunoglobulin molecule of FIG. 13 that was cloned out of the hybridoma E6.2.

FIG. 15 is an amino acid sequence of a kappa light chain immunoglobulin molecule that is secreted by the hybridoma E6.2. Differences between the sequence encoded by light chain variable gene 018 and the sequence of the E6.2 secreted light chain are indicated in bold and enlarged font. The contiguous sequence from CDR1 through CDR3 is indicated by underlining and CDR1, CDR2, and CDR3 sequences are each indicated by double underlining.

FIG. 16 is a nucleotide sequence of the cDNA encoding the kappa light chain immunoglobulin molecule of FIG. 15 that was cloned out of the hybridoma E6.2.

Hybridoma E6.4

The antibody secreted by the hybridoma E6.4 comprises a human IgG2 antibody having a human kappa light chain. The antibodies were analyzed for structural information related to their heavy chain and light chain gene utilization, as well as their amino acid sequences. Thus, heavy chain $V_H$, D, and $J_H$ and light chain Vκ and Jκ gene utilization was analyzed and differences between the coded product and the particular gene utilization was also analyzed. Accordingly, the antibody secreted by the hybridoma E6.4 evidenced the following gene utilization:

V$_H$—4-31
D—A1/A4
J$_H$—4
Vκ—012
Jκ—2

As reported in the V BASE sequence directory, the amino acid sequence encoded by the Vκ012 gene was determined to be:

TITCRASQSISSYLNWYQQKPGKAP-KLLIYAASSLQSGVPSRFSGSGSGTD-FTLTISSLQPEDFATYYCQQSYSTP (SEQ ID NO:21)

Amino acid and nucleotide sequence information respecting the heavy and light chains are provided below in connection with FIGS. 17–20. FIG. 17 is an amino acid sequence of a heavy chain immunoglobulin molecule that is secreted by the hybridoma E6.4. Differences between the sequence encoded by heavy chain variable gene 4-31 and the sequence of the E6.4 secreted heavy chain are indicated in bold and enlarged font. The contiguous sequence from CDR1 through CDR3 is indicated by underlining and CDR1, CDR2, and CDR3 sequences are each indicated by double underlining.

FIG. 18 is a nucleotide sequence of the cDNA encoding the heavy chain immunoglobulin molecule of FIG. 17 that was cloned out of the hybridoma E6.4.

FIG. 19 is an amino acid sequence of a kappa light chain immunoglobulin molecule that is secreted by the hybridoma E6.4. Differences between the sequence encoded by light chain variable gene 012 and the sequence of the E6.4 secreted light chain are indicated in bold and enlarged font. The contiguous sequence from CDR1 through CDR3 is indicated by underlining and CDR1, CDR2, and CDR3 sequences are each indicated by double underlining.

FIG. 20 is a nucleotide sequence of the cDNA encoding the kappa light chain immunoglobulin molecule of FIG. 19 that was cloned out of the hybridoma E6.4.

Hybridoma E2.11

The antibody secreted by the hybridoma E2.11 comprises a human IgG2 antibody having a human kappa light chain. The antibodies were analyzed for structural information related to their heavy chain and light chain gene utilization, as well as their amino acid sequences. Thus, heavy chain V$_H$, D, and J$_H$ and light chain Vκ and Jκ gene utilization was analyzed and differences between the coded product and the particular gene utilization was also analyzed. Accordingly, the antibody secreted by the hybridoma E2.11 evidenced the following gene utilization:

V$_H$—4-61
D—XP1/21-10
J$_H$—4
Vκ—018
Jκ—4

As reported in the V BASE sequence directory, the amino acid sequence encoded by the V$_H$ 4-61 gene was determined to be:

VSGGSVSSGSYYWSWIRQPPGKGLEWI-GYIYYSGSTNYNPSLKSRVTISVDTSKN-QFSLKLSSVTAADTAVYYCAR (SEQ ID NO:22)

Amino acid and nucleotide sequence information respecting the heavy and light chains are provided below in connection with FIGS. 21–24. FIG. 21 is an amino acid sequence of a heavy chain immunoglobulin molecule that is secreted by the hybridoma E2.11. Differences between the sequence encoded by heavy chain variable gene 4-61 and the sequence of the E2.11 secreted heavy chain are indicated in bold and enlarged font. The contiguous sequence from CDR1 through CDR3 is indicated by underlining and CDR1, CDR2, and CDR3 sequences are each indicated by double underlining.

FIG. 22 is a nucleotide sequence of the cDNA encoding the heavy chain immunoglobulin molecule of FIG. 21 that was cloned out of the hybridoma E2.11.

FIG. 23 is an amino acid sequence of a kappa light chain immunoglobulin molecule that is secreted by the hybridoma E2.11. Differences between the sequence encoded by light chain variable gene 018 and the sequence of the E2.11 secreted light chain are indicated in bold and enlarged font. The contiguous sequence from CDR1 through CDR3 is indicated by underlining and CDR1, CDR2, and CDR3 sequences are each indicated by double underlining.

FIG. 24 is a nucleotide sequence of the cDNA encoding the kappa light chain immunoglobulin molecule of FIG. 23 that was cloned out of the hybridoma E2.11.

Hybridoma E6.3

The antibody secreted by the hybridoma E6.3 comprises a human IgG2 antibody having a human kappa light chain. The antibodies were analyzed for structural information related to their heavy chain and light chain gene utilization, as well as their amino acid sequences. Thus, heavy chain V$_H$, D, and J$_H$ and light chain Vκ and Jκ gene utilization was analyzed and differences between the coded product and the particular gene utilization was also analyzed. Accordingly, the antibody secreted by the hybridoma E6.3 evidenced the following gene utilization:

V$_H$—4-61
D—1-2rc
J$_H$—4
Vκ—018
JκK—4

Amino acid and nucleotide sequence information respecting the heavy and light chains are provided below in connection with FIGS. 25–28. FIG. 25 is an amino acid sequence of a heavy chain immunoglobulin molecule that is secreted by the hybridoma E6.3. Differences between the sequence encoded by heavy chain variable gene 4-61 and the sequence of the E6.3 secreted heavy chain are indicated in bold and enlarged font. The contiguous sequence from CDR1 through CDR3 is indicated by underlining and CDR1, CDR2, and CDR3 sequences are each indicated by double underlining.

FIG. 26 is a nucleotide sequence of the cDNA encoding the heavy chain immunoglobulin molecule of FIG. 25 that was cloned out of the hybridoma E6.3.

FIG. 27 is an amino acid sequence of a kappa light chain immunoglobulin molecule that is secreted by the hybridoma E6.3. Differences between the sequence encoded by light chain variable gene 018 and the sequence of the E6.3 secreted light chain are indicated in bold and enlarged font. The contiguous sequence from CDR1 through CDR3 is indicated by underlining and CDR1, CDR2, and CDR3 sequences are each indicated by double underlining.

FIG. 28 is a nucleotide sequence of the cDNA encoding the kappa light chain immunoglobulin molecule of FIG. 27 that was cloned out of the hybridoma E6.3.

Hybridoma E7.6.3

The antibody secreted by the hybridoma E7.6.3 comprises a human IgG2 antibody having a human kappa light chain. The antibodies were analyzed for structural information related to their heavy chain and light chain gene utilization, as well as their amino acid sequences. Thus, heavy chain V$_H$, D, and $J_H$ and light chain Vκ and Jκ gene utilization was analyzed and differences between the coded product and the particular gene utilization was also analyzed. Accordingly, the antibody secreted by the hybridoma E7.6.3 evidenced the following gene utilization:

$V_H$—4-61

D—XP4rc-XP1

$J_H$—3

Vκ—O18

Jκ—4

Amino acid and nucleotide sequence information respecting the heavy and light chains are provided below in connection with FIGS. 29–32. FIG. 29 is an amino acid sequence of a heavy chain immunoglobulin molecule that is secreted by the hybridoma E7.6.3. Differences between the sequence encoded by heavy chain variable gene 4-61 and the sequence of the E7.6.3 secreted heavy chain are indicated in bold and enlarged font. The contiguous sequence from CDR1 through CDR3 is indicated by underlining and CDR1, CDR2, and CDR3 sequences are each indicated by double underlining.

FIG. 30 is a nucleotide sequence of the cDNA encoding the heavy chain immunoglobulin molecule of FIG. 29 that was cloned out of the hybridoma E7.6.3.

FIG. 31 is an amino acid sequence of a kappa light chain immunoglobulin molecule that is secreted by the hybridoma E7.6.3. Differences between the sequence encoded by light chain variable gene O18 and the sequence of the E7.6.3 secreted light chain are indicated in bold and enlarged font. The contiguous sequence from CDR1 through CDR3 is indicated by underlining and CDR1, CDR2, and CDR3 sequences are each indicated by double underlining.

FIG. 32 is a nucleotide sequence of the cDNA encoding the kappa light chain immunoglobulin molecule of FIG. 31 that was cloned out of the hybridoma E7.6.3.

Example 4

Analysis of Heavy and Light Chain Amino Acid Substitutions

Figure 33:
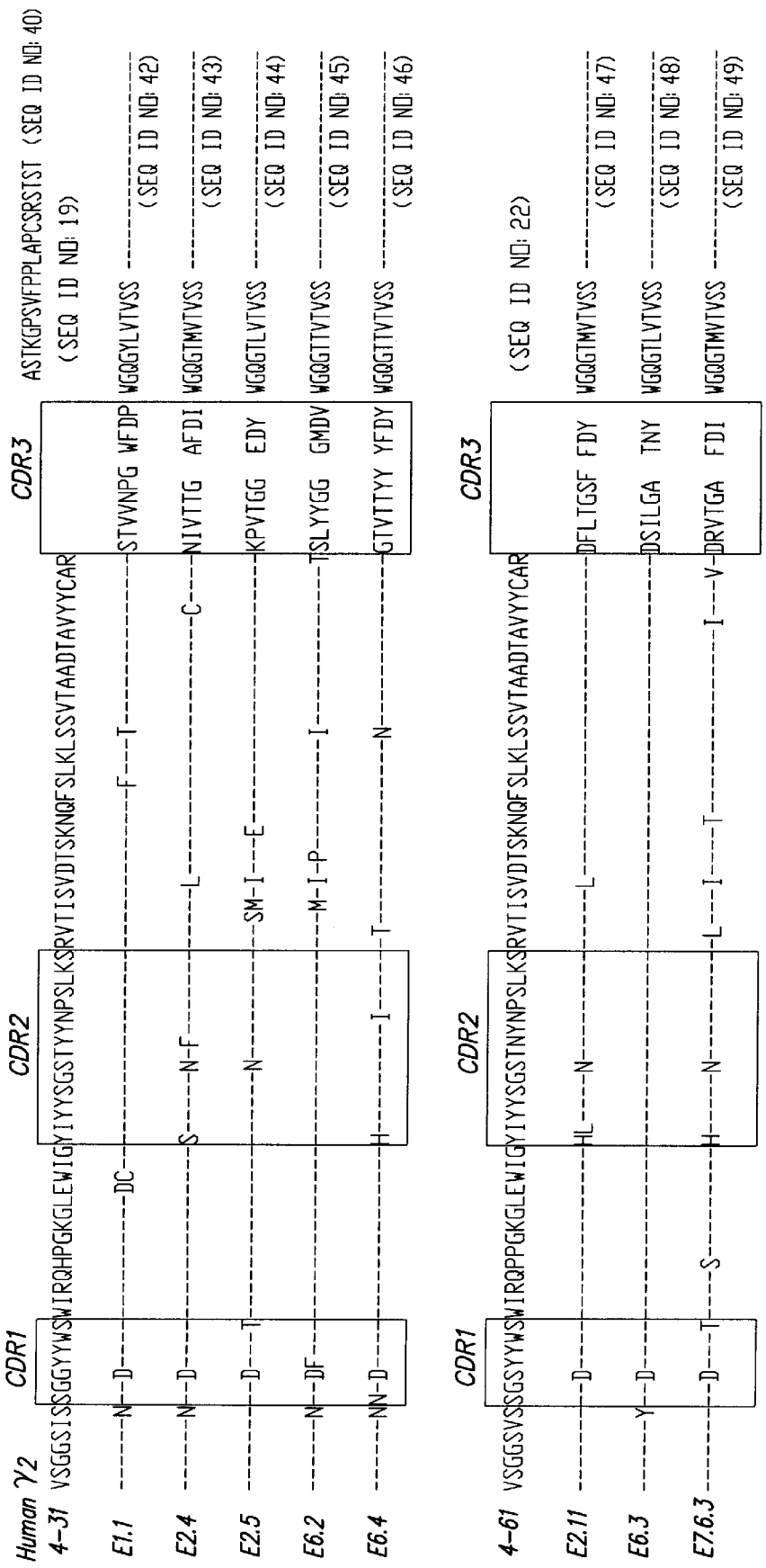
Figure 34:
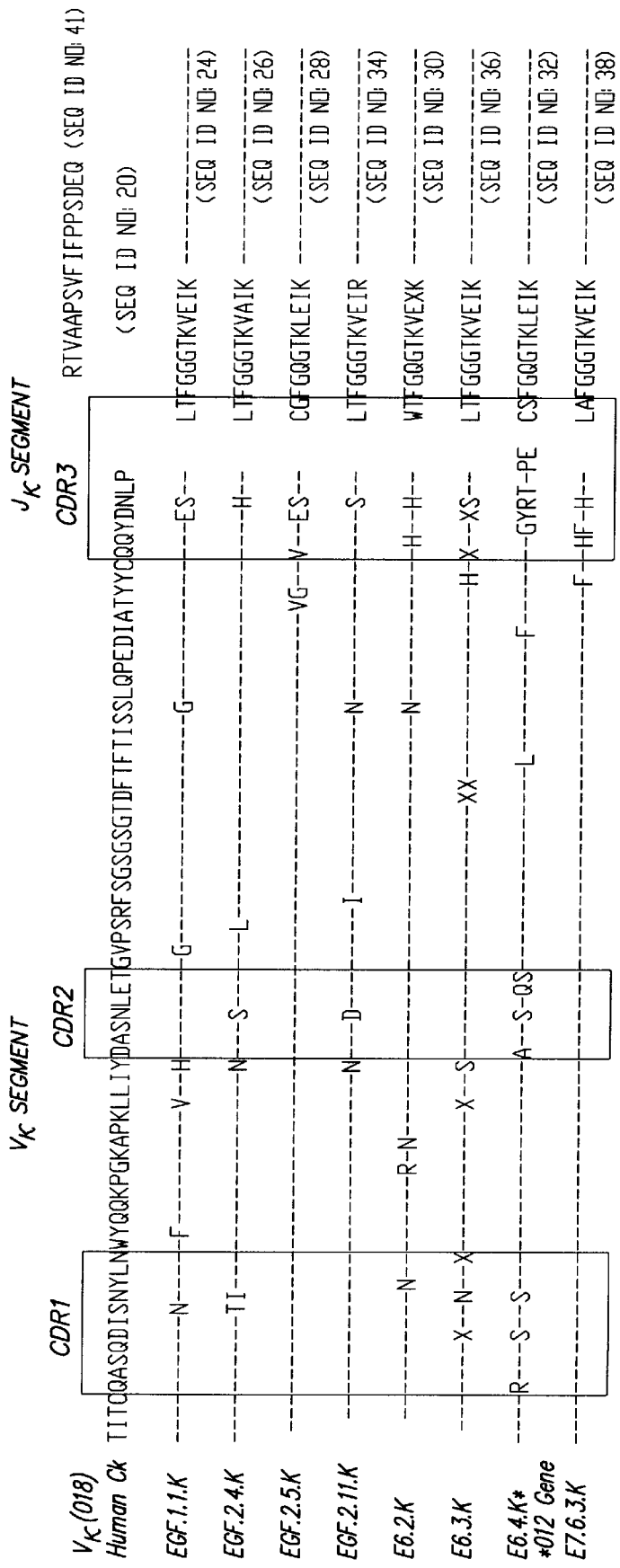

FIG. 33 provides a comparison of specific anti-EGF-r antibody heavy chain amino acid sequence comparisons with the amino acid sequence of the particular $V_H$ gene which encodes the heavy chain of the particular antibody. FIG. 34 provides a similar comparison of specific anti-EGF-r antibody light chain amino acid sequence comparisons with the amino acid sequence of the particular Vκ gene which encodes the light chain of the particular antibody. As will be observed, there are several remarkably conserved amino acid substitutions amongst the heavy and light chain sequences. In particular, in the heavy chains of the antibodies, all of the heavy chain molecules are encoded by $V_H$ 4 family genes and have a Glycine in position 10 in $V_H$ 4-31 encoded antibodies and Serine in position 10 in $V_H$ 4-61 encoded antibodies are each substituted with an Aspartic Acid. Also in the $V_H$ 4-31 heavy chains, all but one of the antibodies includes a Serine in position 7 substitution to Asparagine. A similar, though not quite as predominant substitution is observed in position 35, where a Serine in two of the $V_H$ 4-31 encoded antibodies and two of the $V_H$ 4-61 encoded antibodies is substituted with an Asparagine. Also, in two of the $V_H$ 4-31 encoded antibodies and two of the $V_H$ 4-61 encoded antibodies there are substitutions at position 28, where in each case, a Tyrosine is substituted with a Serine (E2.4) or a Histidine (E6.4, E2.11, and E7.6.3). Five of the antibodies, three of the $V_H$ 4-31 encoded antibodies and two of the $V_H$ 4-61 encoded antibodies, possess Valine to Leucine (E2.4 and E2.11) or Isoleucine (E2.5, E6.2, and E7.6.3) at position 50.

In connection with the kappa light chains amino acid sequences, all of the sequences are encoded by Vκ I family genes, with seven of the molecules being encoded by O18 genes and one (E6.4) being encoded by an O12 gene. There is a high degree of homology between the O12 and O18 gene products, as evidenced when the E6.4 molecule is compared with the O18 gene product, along with the other molecules, in FIG. 34. The E6.4 molecule possesses only two substitutions relative to the O12 gene product, as shown in FIG. 19, and only 13 substitutions relative to the O18 gene product. All of the antibodies possess a substitution at position 74 in CDR3 where an Asparagine is substituted with a Serine (E1.1, E2.5, E2.11, and E6.3), Histidine (E2.4, E6.2, and E7.6.3), or Arginine (E6.4). The remainder of the substitutions are less highly conserved. However, a number of the antibodies appear to possess substitutions within the CDR's. However, it is interesting to note that E7.6.3, which is an antibody with very high affinities, possesses no amino acid substitutions in the light chain amino acid sequence until just proximal to CDR3 and within CDR3.

It will be appreciated that each of the above-identified amino acid substitutions exist in close proximity to or within a CDR. Such substitutions would appear to bear some effect upon the binding of the antibody to the EGF receptor molecule. Further, such substitutions could have significant effect upon the affinity of the antibodies.

As was discussed above, anti-EGF-r antibodies have been demonstrated to possess certain anti-tumor activities. The following experiments were carried out in order to determine if antibodies in accordance with the present invention possessed such anti-tumor activities.

Example 5

Blockage of EGF and TGF-α Binding to Human Epidermoid Carcinoma A431 Cells by Human Anti-EGF-r Antibodies in vitro An in vitro assay was conducted to determine if antibodies in accordance with the present invention were capable of blocking EGF binding to a human carcinoma cell line. The experiment was conducted to compare the binding of antibodies in accordance with the invention with the murine monoclonal antibody 225 which, as discussed above, has previously demonstrated anti-cancer activity.

Figure 35:
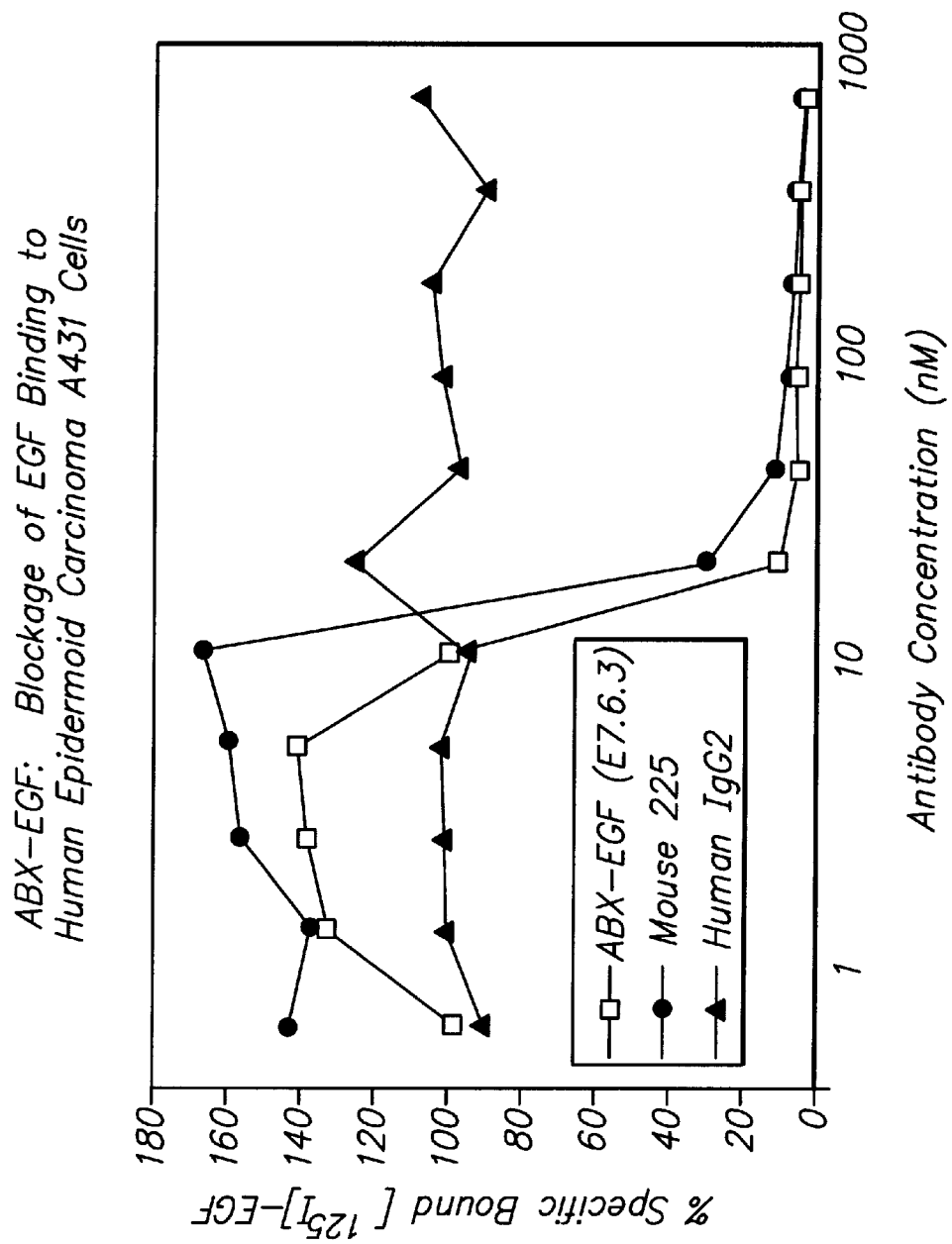

In this example, the human epidermoid carcinoma A431 cell line was utilized. The A431 cell line is known for its high expression level of EGF-r (about $2 \times 10^6$ EGF-r molecules per cell). Therefore, higher concentrations of anti-EGF-r antibodies are required to saturate all of the binding sites. The results from this example are shown in FIG. 35. In the Figure, blockage of $I^{125}$ labeled EGF binding to human epidermoid carcinoma A431 cells by a human anti-EGF-r antibody in vitro is demonstrated. In the Figure, (□) depicts the results achieved by the anti-EGF-r antibody in accordance with the invention (E7.6.3), (○) depicts the results achieved by the murine monoclonal antibody 225, and (▲) depicts the results achieved by a control, nonspecific, human IgG2 antibody.

Figure 36:
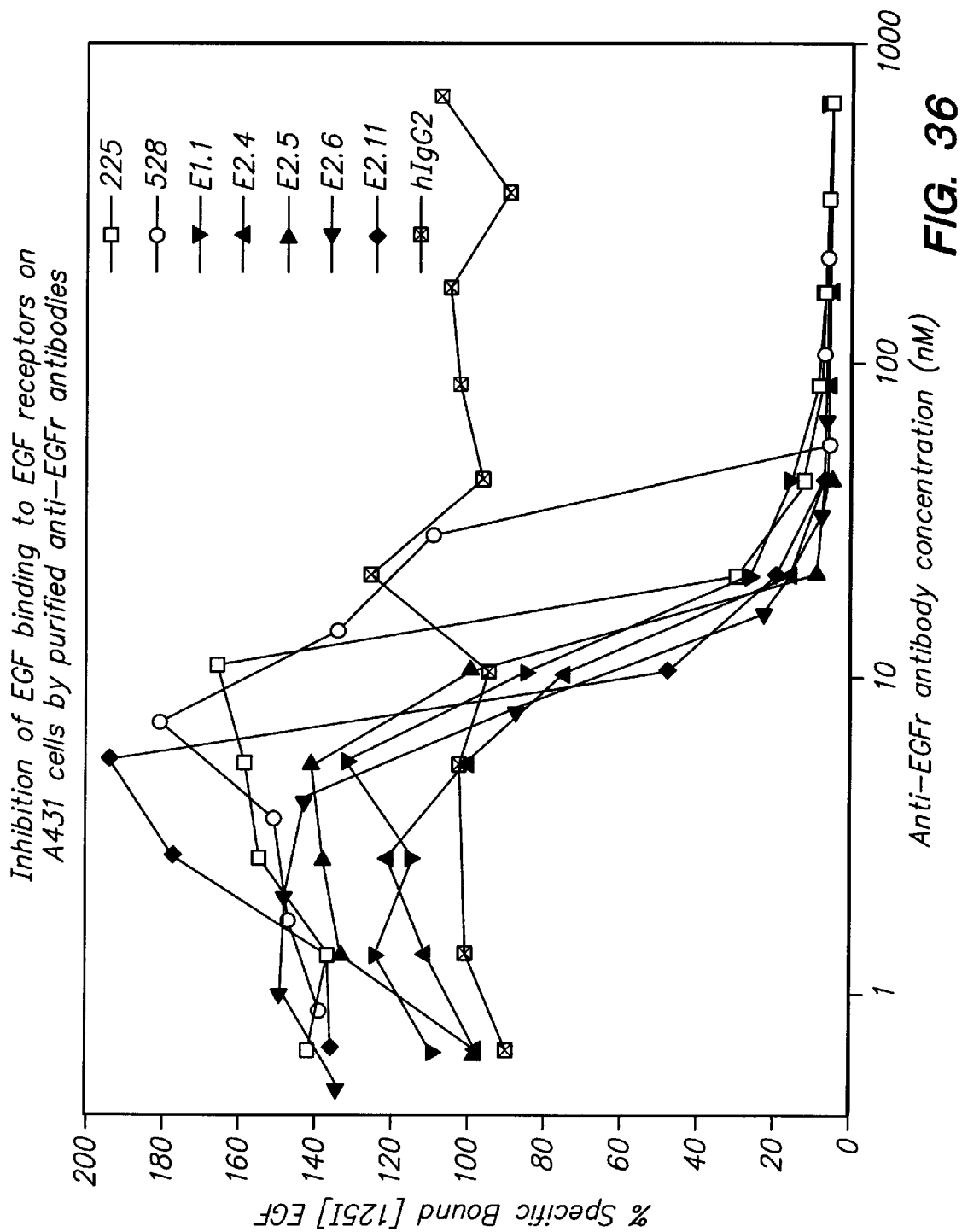

FIG. 36 shows inhibition of EGF binding to human epidermoid carcinoma A431 cells by a panel of human anti-EGF-r antibodies in accordance with the invention in vitro when compared to the 225, 528, and nonspecific human IgG2 controls. In the Figure, (□) depicts the results achieved by the murine monoclonal antibody 225, (○) depicts the results achieved by the murine monoclonal antibody 528, (▼) depicts the results achieved using the E1.1 antibody in accordance with the invention, (▲) depicts the results achieved using the E2.4 antibody in accordance with the invention, (▶) depicts the results achieved using the E2.5 antibody in accordance with the invention, (◀) depicts the results achieved using the E2.6 antibody in accordance with the invention, (♦) depicts the results achieved using the E2.11 antibody in accordance with the invention, and (▩) depicts the results achieved using a control, nonspecific human IgG2 antibody.

The results indicate that antibodies in accordance with the invention may block EGF binding to surface expressed EGF-r on A431 cells better than the 225 and 528 antibodies. Antibodies in accordance with the invention appear to begin inhibiting binding at an 8 nM concentration as compared to a 10 nM concentration for the 225 antibody.

Figure 37:
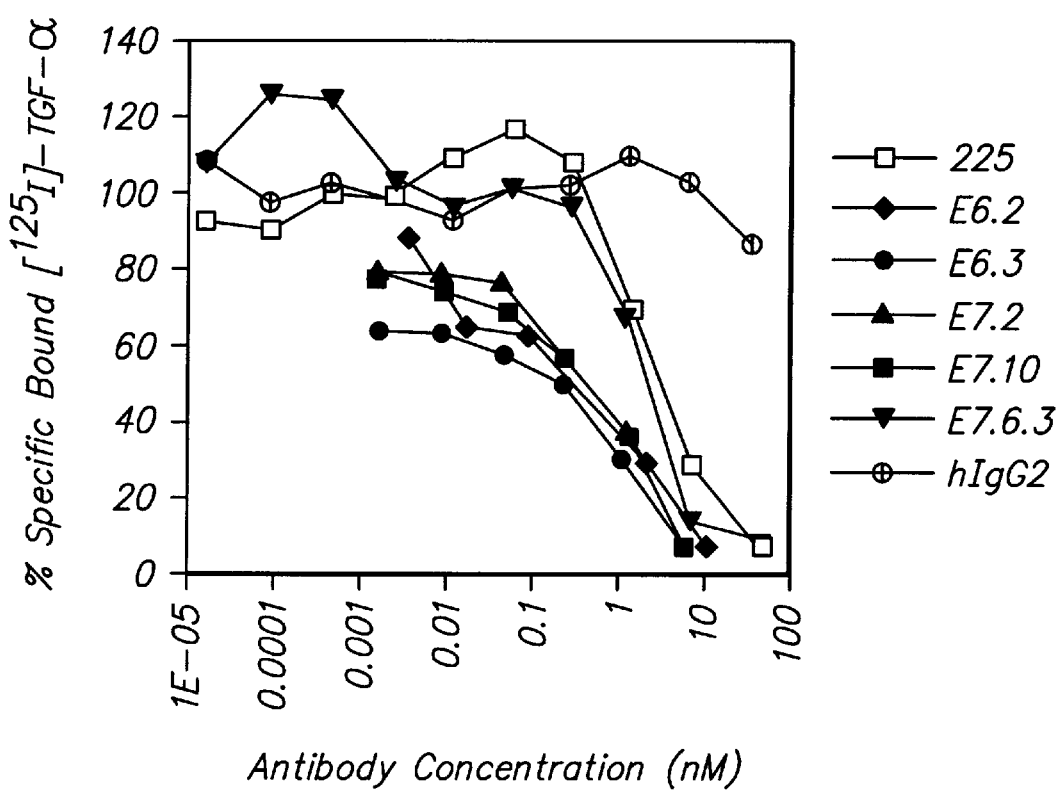

In connection with inhibition of TGF-α binding, similar efficacy is observed through use of antibodies in accordance with the invention when compared to the 225 antibody. FIG. 37 shows inhibition of TGF-α binding to human epidermoid carcinoma A431 cells by human anti-EGF-r antibodies in vitro, where (□) depicts the results achieved by the murine monoclonal antibody 225, (♦) depicts the results achieved using the E6.2 antibody in accordance with the invention, (●) depicts the results achieved using the E6.3 antibody in accordance with the invention, (▲) depicts the results achieved using the E7.2 antibody in accordance with the invention, (■) depicts the results achieved using the E7.10 antibody in accordance with the invention, (▼) depicts the results achieved using the E7.6.3, and (✪) depicts the results achieved using a control, nonspecific human IgG2 antibody.

The results indicate that antibodies in accordance with the invention may block TGF-α binding to surface expressed EGF-r on A431 cells better than the 225 antibody. Antibodies in accordance with the invention appear to begin inhibiting binding at an 0.1 nM concentration as compared to a 1 nM concentration for the 225 antibody.

Example 6

Blockage of EGF Binding to Human Colon Adenocarcinoma SW948 Cells by Human Anti-EGF-r Antibodies in vitro Another in vitro assay was conducted to determine if antibodies in accordance with the present invention were capable of blocking EGF binding to yet another human carcinoma cell line. The experiment was conducted to compare the binding of antibodies in accordance with the invention with the murine monoclonal antibody 225 which, as discussed above, has previously demonstrated anti-cancer activity.

In this example, the human colon adenocarcinoma SW948 cell line was utilized. In contrast to the A431 cell line, the SW948 cell line has relatively low expression of EGF-r on its surface (about 40,000 molecules per cell). Therefore, less of the anti-EGF-r antibodies are required to saturate all of the binding sites of the receptors on the cells. The results from this example are shown in FIG. 38. In the Figure, blockage of $I^{125}$ labeled EGF binding to human colon adenocarcinoma SW948 cells by a human anti-EGF-r antibody in vitro is demonstrated. In the Figure, (○) depicts the results achieved by an anti-EGF-r antibody in accordance with the invention (E7.6.3), (□) depicts the results achieved by the murine monoclonal antibody 225, and (▲) depicts the results achieved by a control, nonspecific, human IgG2 antibody.

The results indicate that the antibody in accordance with the invention blocks EGF binding to SW948 cells at least as well as the 225 antibody. In fact, the curve is slightly improved with respect to the antibody in accordance with the invention, showing inhibition at lower concentrations than the 225 antibody.

Example 7

Inhibition of Human Colon Adenocarcinoma SW948 Cell Growth by Human Anti-EGF-r Antibodies in vitro We also conducted an in vitro assay to determine whether and to what degree, as compared to the 225 antibody, antibodies in accordance with the invention were capable of inhibiting cancer cell growth. The experiment was conducted to compare the inhibition by antibodies in accordance with the invention with the inhibition by the murine monoclonal antibody 225 which, as discussed above, has previously demonstrated anti-cancer activity.

In this example, the human colon adenocarcinoma SW948 cell line was utilized. In our hands, only the SW948 cell line showed EGF-dependent cell growth. In contrast, the A431 cell line showed growth inhibition in the presence of EGF in vitro. The results are shown in FIG. 39 where it is demonstrated that human anti-EGF-r antibodies in accordance with the present invention inhibit the growth of SW948 cells in vitro. In the Figure, (○) depicts the results achieved by an anti-EGF-r antibody in accordance with the invention (E7.6.3), (□) depicts the results achieved by the murine monoclonal antibody 225, and (▲) depicts the results achieved by a control, nonspecific, human IgG2 antibody.

The results indicate that the antibody in accordance with the invention inhibits growth of SW948 cells at least as well as the 225 antibody. In fact, the curve is slightly improved with respect to the antibody in accordance with the invention, showing an apparent 100% inhibition in cell growth at approximately 100 μg/ml whereas the 225 antibody appears to plateau at an inhibition level between 80 to 90% in the same dosage range.

Example 8

Inhibition of Human Epidermoid Carcinoma Growth in Nude Mice by Human Anti-EGF-r Antibodies in vivo In the present experiment, we sought to determine if antibodies in accordance with the present invention were capable of inhibiting tumor cell growth in vivo. In the experiment, nude mice at the age of 8 weeks were inoculated subcutaneously with the human epidermoid carcinoma A431 cell line. Mice were injected with $5 \times 10^6$ A431 cells. One of two dosages of an antibody in accordance with the invention or one of two controls was injected intraperitoneally on the same day when the A431 cells were inoculated. Three adminstrations of either antibody or control followed and mice were followed for subcutaneous tumor formation and size. The dosages of antibody utilized were either 1.0 mg or 0.2 mg. The controls were either phosphate buffered saline or a nonspecific human IgG2 antibody.

The results from this experiment are shown in FIG. 40. In the Figure, the inhibition of human epidermoid carcinoma cell growth in nude mice through use of human anti-EGF-r antibodies in accordance with the invention in vivo is evident. In the Figure, (▲) depicts the results achieved with a dosage of 1.0 mg of a human anti-EGF-r antibody in accordance with the present invention (E7.6.3) (n=5), (▼)depicts the results achieved with a dosage of 0.2 mg of the E.7.6.3 antibody (n=4), (□) depicts the results achieved by a control, nonspecific, human IgG2 antibody (n=6), and (○) depicts the results achieved utilizing phosphate buffered saline as a control (n=6).

No tumor growth was observed in animals treated with the E7.6.3 antibody whereas control animals grew significant tumors within 25 days of tumor cell inoculation.

In the same experiment, three antibodies in accordance with the invention were compared. The results are shown in FIG. 41. Each of the antibodies in accordance with the present invention, E7.6.3 at 1 mg in 5 mice and 0.2 mg in 4 mice, E2.5 at 1 mg in 3 mice and 0.2 mg in 3 mice, and E1.1 at 1 mg in 3 mice, demonstrated inhibition of the human epidermoid carcinoma formation in the mice in comparison to controls. All of the control animals (including 6 PBS-treated animals and 6 human IgG2-treated animals) developed significant tumors within 19 days of inoculation whereas none of the the animals treated with the human anti-EGF-r antibodies in accordance with the invention developed tumors within 19 days of inoculation.

FIG. 42 shows the results of following the animals from this above-mentioned same experiment for 130 days post inoculation with the human epidermoid carcinoma. The results from this experiment are shown in FIG. 42. In the Figure, it will be observed that all of the control mice had developed tumors within 20 days of tumor cell inoculation. In contrast, the first mouse treated with an antibody in accordance with the present invention to develop a tumor was on day 70. By day 130, only 4 out of 15 of the experimental animals had developed tumors. Interestingly, none of the experimental animals treated with the 0.2 mg dosage of the E2.5 antibody developed tumors within the test period.

The above experiment in connection with this Example 8 demonstrate that antibodies in accordance with the present invention if administered contemporaneously with the inoculation of a tumor cell line appear to almost entirely prevent the initiation of tumor cell growth and initiation of the tumor. Moreover, it will be observed that the inhibitory effect on tumor cell growth appears long-lasting.

Example 9

Eradication of Human Epidermoid Carcinoma Growth in Nude Mice by Human Anti-EGF-r Antibodies in vivo While preventing tumor cell growth and/or establishment of a tumor, as discussed above in connection with the preceding example, is a positive finding, from a therapeutic point of view, eradication of an established tumor is also highly desirable. Accordingly, in the following experiments we examined whether antibodies in accordance with the invention were capable of eradicating an established tumor in a mammal. Previous data generated in connection with the 225 antibody indicated that in order to effectively eradicate an established tumor through use of the 225 antibody it was necessary to complement treatment with an antineoplastic agent. Thus, in connection with our experiments, we looked at antibody treatment both alone and in combination with antineoplastic agent treatment.

In the experiment, nude mice were inoculated subcutaneously with $5 \times 10^6$ A431 human epidermoid carcinoma cells on day 0. Mice were treated with either antibodies, chemotherapeutic agents, and/or controls after the tumor had an opportunity to become established (size $\geq 0.4$ cm$^3$). Treatments were begun and continued on days 5, 8, 10, 14, 16, and 21, with chemotherapies being administered only on days 5 and 6. Therapies consisted of an antibody in accordance with the invention (E7.6.3), the antineoplastic agent doxorubicin, and a combination of antibody and doxorubicin. Controls were phosphate buffered saline or a nonspecific human IgG2 antibody. Each treatment group consisted of 5 animals. The data generated from the experiments are shown in FIG. 43, where (▲) depicts the results achieved with a dosage of 1 mg of a human anti-EGF-r antibody in accordance with the present invention (E7.6.3) (n=5), (X) depicts the results achieved with a dosage of 125 μg of doxorubicin, (*) depicts the results achieved with a dosage of 1 mg of a human anti-EGF-r antibody in accordance with the present invention (E7.6.3) in combination with a dosage of 125 μg of doxorubicin, (■) depicts the results achieved by a control, nonspecific, human IgG2 antibody, and (♦) depicts the results achieved utilizing phosphate buffered saline as a control.

As will be observed, administration of the E7.6.3 antibody in combination with doxorubicin resulted in complete eradication tumor growth. Further, tumor growth was completely arrested through administration of the E7.6.3 antibody alone.

In a similar experiment, the results of which are shown in FIG. 44, following inoculation with the tumor, five mice were treated with 0.5 mg of the E2.5 antibody on days 5, 8, 10, 14, 16, and 21 and five mice were treated with a combination of the E2.5 antibody administered on days 5, 8, 10, 14, 16, and 21 and doxorubicin administered on days 5 and 6. In the Figure, (♦) depicts the results achieved with a dosage of 0.5 mg of a human anti-EGF-r antibody in accordance with the present invention (E2.5), (■) depicts the results achieved with a dosage of 125 μg of doxorubicin, (▲) depicts the results achieved with a dosage of 0.5 mg of a human anti-EGF-r antibody in accordance with the present invention (E2.5) in combination with a dosage of 125 μg of doxorubicin, (X) depicts the results achieved utilizing phosphate buffered saline as a control, and (*) depicts the results achieved utilizing a control, nonspecific, human IgG2 antibody.

As will be observed, administration of the E2.5 antibody by itself, or in combination with doxorubicin, resulted in near complete eradication of tumors in the mice.

Example 10

Human Clinical Trials for the Treatment and Diagnosis of Human Carcinomas through use of Human Anti-EGF-r Antibodies in vivo Introduction Antibodies in accordance with the present invention are indicated in the treatment of certain solid tumors. Based upon a number of factors, including EGF-r expression levels, among others, the following tumor types appear to present preferred indications: breast, ovarian, colon, prostate, bladder and non-small cell lung cancer. In connection with each of these indications, three clinical pathways appear to offer distinct potentials for clinical success:

Adjunctive therapy: In adjunctive therapy, patients would be treated with antibodies in accordance with the present invention in combination with a chemotherapeutic or antineoplastic agent and/or radiation therapy. The primary targets listed above will be treated under protocol by the addition of antibodies of the invention to standard first and second line therapy. Protocol designs will address effectiveness as assessed by reduction in tumor mass as well as the ability to reduce usual doses of standard chemotherapy. These dosage reductions will allow additional and/or prolonged therapy by reducing dose-related toxicity of the chemotherapeutic agent. Prior art anti-EGF-r antibodies have been, or are being, utilized in several adjunctive clinical trials in combination with the chemotherapeutic or antineoplastic agents adriamycin (C225: advanced prostrate carcinoma), cisplatin (C225: advanced head and neck and lung carcinomas), taxol (C225: breast cancer), and doxorubicin (C225: preclinical).

Monotherapy: In connection with the use of the antibodies in accordance with the present invention in monotherapy of tumors, the antibodies will be adminstered to patients without a chemotherapeutic or antineoplastic agent. Preclinical results generated through use of antibodies in accordance with the present invention and discussed herein have demonstrated similar results with both adjunctive therapy and/or as a stand-alone therapy. Moreover, monotherapy has apparently been conducted clinically in end stage cancer patients with extensive metastatic disease. Patients appeared to show some disease stabilization. Id. Trials will be designed to demonstrate an effect in refractory patients with (cancer) tumor.

Imaging Agent: Through binding a radionuclide (e.g., yttrium ($^{90}$Y)) to antibodies in accordance with the present invention, it is expected that radiolabeled antibodies in accordance with the present invention can be utilized as a diagnostic, imaging agent. In such a role, antibodies of the invention will localize to both solid tumors, as well as, metastatic lesions of cells expressing the EGF receptor. In connection with the use of the antibodies of the invention as imaging agents, the antibodies can be used in assisting surgical treatment of solid tumors, as both a pre-surgical screen as well as a post operative follow to determine what tumor remain and/or returns. An ($^{111}$In)-C225 antibody has been used as an imaging agent in a Phase I human clinical trial in patients having unresectable squamous cell lung carcinomas. Divgi et al. *J. Natl. Cancer Inst.* 83:97–104 (1991). Patients were followed with standard anterior and posterior gamma camera. Preliminary data indicated that all primary lesions and large metastatic lestions were identified, while only one-half of small metastatic lesions (under 1 cm) were detected.

Dose and Route of Administration

While specific dosing for antibodies in accordance with the invention has not yet been determined, certain dosing considerations can be determined through comparison with the similar product (ImClone C225) that is in the clinic. The C225 antibody is typically being administered with doses in the range of 5 to 400 mg/m$^2$, with the lower doses used only in connection with the safety studies. Antibodies in accordance with the invention have a one-log higher affinity than the C225 antibody. Further, antibodies in accordance with the present invention are fully human antibodies, as compared to the chimeric nature of the C225 antibody and, thus, antibody clearance would be expected to be slower. Accordingly, we would expect that dosing in patients with antibodies in accordance with the invention can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are expected to be useful for delivery of the antibodies in accordance with the invention. Conventional intravenous delivery will presumably be the standard delivery technique for the majority of tumors. However, in connection with tumors in the peritoneal cavity, such as tumors of the ovaries, biliary duct, other ducts, and the like, intraperitoneal administration may prove favorable for obtaining high dose of antibody at the tumor and to minimize antibody clearance. In a similar manner certain solid tumors possess vasculature that is appropriate for regional perfusion. Regional perfusion will allow the obtention of a high dose of the antibody at the site of a tumor and will minimize short term clearance of the antibody.

Clinical Development Plan (CDP)

Overview: The CDP will follow and develop treatments of anti-EGF-r antibodies in accordance with the invention in connection with adjunctive therapy, monotherapy, and as an imaging agent. Trials will be initially utilized to demonstrate safety and will thereafter be utilized to address efficacy in repeat doses. Trails will be open label comparing standard chemotherapy with standard therapy plus antibodies in accordance with the invention. As will be appreciated, one criteria that can be utilized in connection with enrollment of patients can be EGF-r expression levels of patient tumors as determined in biopsy.

As with any protein or antibody infusion based therapeutic, safety concerns are related primarily to (i) cytokine release syndrome, i.e., hypotension, fever, shaking, chills, (ii) the development of an immunogenic response to the material (i.e., development of human antibodies by the patient to the human antibody therapeutic, or HAHA response), and (iii) toxicity to normal cells that express the EGF receptor, e.g., hepatocytes which express EGF-r. Standard tests and follow up will be utilized to monitor each of these safety concerns. In particular, liver function will be monitored frequently during clinical trails in order to assess damage to the liver, if any.

Human Clinical Trial Adjunctive Therapy with Human Anti-EGF-r Antibody and Chemotherapeutic Agent A phase I human clinical trial will be initiated to assess the safety of six intravenous doses of a human anti-EGF-r antibody in accordance with the invention in connection with the treatment of a solid tumor, e.g., breast cancer. In the study, the safety of single doses of antibodies in accordance with the invention when utilized as an adjunctive therapy to an antineoplastic or chemotherapeutic agent, such as cisplatin, topotecan, doxorubicin, adriamycin, taxol, or the like, will be assessed. The trial design will include delivery of six, single doses of an antibody in accordance with the invention with dosage of antibody escalating from approximately about 25 mg/m$^2$ to about 275 mg/m$^2$ over the course of the treatment in accordance with the following schedule:

|  | Day 0 | Day 7 | Day 14 | Day 21 | Day 28 | Day 35 |
|---|---|---|---|---|---|---|
| Mab Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients will be closely followed for one-week following each administration of antibody and chemotherapy. In particular, patients will be assessed for the safety concerns mentioned above: (i) cytokine release syndrome, i.e., hypotension, fever, shaking, chills, (ii) the development of an immunogenic response to the material (i.e., development of human antibodies by the patient to the human antibody therapeutic, or HAHA response), and (iii) toxicity to normal cells that express the EGF receptor, e.g., hepatocytes which express EGF-r. Standard tests and follow up will be utilized to monitor each of these safety concerns. In particular, liver function will be monitored frequently during clinical trails in order to assess damage to the liver, if any.

Patients will also be assessed for clinical outcome, and particularly reduction in tumor mass as evidenced by MRI or other imaging.

Assuming demonstration of safety and an indication of efficacy, Phase II trials would likely be initiated to further explore the efficacy and determine optimum dosing.

Human Clinical Trial: Monotherapy with Human Anti-EGF-r Antibody

Assuming that the antibodies in accordance with the present invention appear safe in connection with the above-discussed adjunctive trial, a human clinical trial to assess the efficacy and optimum dosing for monotherapy. Such trial could be accomplished, and would entail the same safety and outcome analyses, to the above-described adjunctive trial with the exception being that patients will not receive chemotherapy concurrently with the receipt of doses of antibodies in accordance with the invention.

Human Clinical Trial: Diagnostic Imaging with Anti-EGF-r Antibody

Once again, assuming that the adjunctive therapy discussed above appears safe within the safety criteria discussed above, a human clinical trial can be conducted concerning the use of antibodies in accordance with the present invention as a diagnostic imaging agent. It is expected that the protocol would be designed in a substantially similar manner to that described in Divgi et al. *J. Natl. Cancer Inst.* 83:97–104 (1991).

INCORPORATION BY REFERENCE

All references cited herein, including patents, patent applications, papers, text books, and the like, and the references cited therein, to the extent that they are not already, are hereby incorporated herein by reference in their entirety. In addition, the following references are also incorporated by reference herein in their entirety, including the references cited in such references:

Abertsen et al., "Construction and characterization of a yeast artificial chromosome library containing seven haploid human genome equivalents." *Proc. Natl. Acad. Sci.* 87:4256 (1990).

Anand et al., "Construction of yeast artificial chromosome libraries with large inserts using fractionation by pulsed-field gel electrophoresis." *Nucl. Acids Res.* 17:3425–3433 (1989).

Berman et al. "Content and organization of the human Ig VH locus: definition of three new $V_H$ families and linkage to the Ig $C_H$ locus." *EMBO J.* 7:727–738 (1988).

Brezinschek et al., "Analysis of the heavy chain repertoire of human peripheral B-cells using single-cell polymerase chain reaction." *J. Immunol.* 155:190–202 (1995).

Brownstein et al., "Isolation of single-copy human genes from a library of yeast artificial chromosome clones." *Science* 244:1348–1351 (1989).

Bruggeman et al. *PNAS USA* 86:6709–6713 (1989).

Bruggemann et al., "Human antibody production in transgenic mice: expression from 100 kb of the human IgH locus." *Eur. J. Immunol.* 21:1323–1326 (1991).

Bruggeman, M. and Neuberger, M. S. in *Methods: A companion to Methods in Enzymology* 2:159–165 (Lerner et al. eds. Academic Press (1991)).

Bruggemann, M. and Neuberger, M. S. "Strategies for expressing human antibody repertoires in transgenic mice." *Immunology Today* 17:391–397 (1996).

Chen et al. "Immunoglobulin gene rearrangement in B-cell deficient mice generated by targeted deletion of the $J_H$ locus" *International Immunology* 5:647–656 (1993)

Choi et al. "Transgenic mice containing a human heavy chain immunoglobulin gene fragment cloned in a yeast artificial chromosome" *Nature Genetics* 4:117–123 (1993)

Coligan et al., Unit 2.1, "Enzyme-linked immunosorbent assays," in *Current protocols in immunology* (1994).

Cook, G. P. and Tomlinson, I. M., "The human immunoglobulin $V_H$ repertoire." *Immunology Today* 16:237–242 (1995).

Cox et al., "A directory of human germ-line Vx segments reveals a strong bias in their usage." *Eur. J. Immunol.* 24:827–836 (1994).

Dariavach et al., "The mouse IgH 3'-enhancer." *Eur. J. Immunol.* 21:1499–1504 (1991).

Den Dunnen et al., "Reconstruction of the 2.4 Mb human DMD-gene by homologous YAC recombination." *Human MolecularGenetics* 1: 19–28 (1992).

Feeney, A. J. "Lack of N regions in fetal and neonatal mouse immunoglobulin V-D-J junctional sequences." *J. Exp. Med.* 172:137–1390 (1990).

Fishwild et al., "High-avidity human IgGκmonoclonal antibodies from a novel strain of minilocus transgenic mice." *Nature Biotech.* 14:845–851 (1996).

Flanagan, J. G. and Rabbitts, T. H., "Arrangement of human immunoglobulin heavy chain constant region genes implies evolutionary duplication of a segment containing g, e, and a genes." *Nature* 300:709–713 (1982).

Galfre, G. and Milstein, C., "Preparation of monoclonal antibodies: strategies and procedures." *Methods Enzymol.* 73:3–46 (1981).

Gemmill et al., "Protocols for pulsed field gel electrophoresis: Separation and detection of large DNA molecules." *Advances in Genome Biology* 1:217–251 (1991).

Gill et al., "Monoclonal anti-epidermal growth factor receptor antibodies which are inhibitors of epidermal growth factor binding and antagonists of epidermal growth factorstimulated tyrosine protein kinase activity." *J. Biol. Chem.* 259:7755 (1984).

Green et al., "Antigen-specific human monoclonal antibodies from mice engineered with human Ig heavy and light chain YACs." *Nature Genetics* 7:13–21 (1994).

Hermanson et al., "Rescue of end fragments of yeast artificial chromosomes by homologous recombination in yeast." *Nucleic Acids Res.* 19:4943–4948 (1991).

Huber et al., "The human immunoglobulin κ locus. Characterization of the partially duplicated L regions." *Eur. J. Immunol.* 23:2860–2967 (1993).

Jakobovits, A., "Humanizing the mouse genome." *Current Biology* 4:761–763 (1994).

Jakobovits, A., "Production of fully human antibodies by transgenic mice." *Current Opinion in Biotechnology* 6:561–566 (1995).

Jakobovits et al., "Germ-line transmission and expression of a human-derived yeast artificial-chromosome." *Nature* 362:255–258 (1993).

Jakobovits, A. et al., "Analysis of homozygous mutant chimeric mice: Deletion of the immunoglobulin heavy-chain joining region blocks B-cell development and antibody production." *Proc. Natl. Acad. Sci. USA* 90:2551–2555 (1993).

Kawamoto et al., "Growth stimulation of A431 cells by epidermal growth factor: Identification of high affinity receptors for EGF by an anti-receptor monoclonal antibody." *Proc. Nat. Acad. Sci., USA* 80:1337–1341 (1983).

Lonberg et al., "Antigen-specific human antibodies from mice comprising four distinct genetic modifications." *Nature* 368:856–859 (1994).

Lusti-Marasimhan et al., "Mutation of Leu25 and Val27 introduces CC chemokine activity into interleukin-8." *J. Biol. Chem.* 270:2716–2721 (1995).

Marks et al., "Oligonucleotide primers for polymerase chain reaction amplification of human immunoglobulin variable genes and design of family-specific oligonucleotide probes." *Eur. J. Immunol.* 21:985–991 (1991).

Matsuda et al., "Structure and physical map of 64 variable segments in the 3' 0.8-megabase region of the human immunoglobulin heavy-chain locus." *Nature Genetics* 3:88–94 (1993).

Max, E. *Molecular genetics of immunoglobulins. Fundamental Immunology.* 315–382 (Paul, W E, ed., New York: Raven Press (1993)).

Mendez et al., "A set of YAC targeting vectors for the interconversion of centric and acentric arms." *Cold Spring Harbor Laboratory Press, Genome Mapping and Sequencing meeting,* 163 (1993).

Mendez et al., "Analysis of the structural integrity of YACs comprising human immunoglobulin genes in yeast and in embryonic stem cells." *Genomics* 26:294–307 (1995).

Ray, S. and Diamond, B., "Generation of a fusion partner to sample the repertoire of Splenic B-cells destined for apoptosis." *Proc. Natl. Acad. Sci. USA* 91:5548–5551 (1994).

Sato et al., "Biological effects in vitro of monoclonal antibodies to human epidermal growth factor receptors" *Mol. Biol. Med.* 1:511–529 (1983).

Schiestl, R. H. and Gietz, R. D., "High efficiency transformation of intact yeast cells using stranded nucleic acids as a carrier." *Curr. Genet.* 16:339–346 (1989).

Sherman et al., "Laboratory Course Manual for Methods in Yeast Genetics." (Cold Spring Harbor Laboratory Press, Cold Spring Harbor, N.Y. (1986)).

Silverman et al., "Meiotic recombination between yeast artificial chromosomes yields a single clone containing the entire BCL2 protooncogene." *Proc. Natl. Acad. Sci. USA* 87:9913–9917 (1990).

Srivastava, A. and Schlessinger, D., "Vectors for inserting selectable markers in vector arms and human DNA inserts of yeast artificial chromosomes (YACs)." *Gene* 103:53–59 (1991).

Taylor et al., "A transgenic mouse that expresses a diversity of human sequence heavy and light chain immunoglobulins." *Nucleic Acids Research* 20:6287–6295 (1992).

Taylor et al., "Human immunoglobulin transgenes undergo rearrangement, somatic mutation and class switching in mice that lack endogenous IgM." *International Immunology* 6:579–591 (1994).

Tuaillon et al., "Human immunoglobulin heavy-chain minilocus recombination in transgenic mice: gene-segment use in m and g transcripts." *Proc. Natl. Acad. Sci. USA* 90:3720–3724 (1993).

Tuaillon et al. "Analysis of direct and inverted $DJ_H$ rearrangements in a human Ig heavy chain transgenic minilocus" *J. Immunol.* 154:6453–6465 (1995)

Vaughan et al., "Human antibodies with subnanomolar affinities isolated from a large non-immunized phage display library." *Nature Biotech.* 14:309–314 (1996).

Wagner et al., "The diversity of antigen-specific monoclonal antibodies from transgenic mice bearing human immunoglobulin gene miniloci." *Eur. J. Immunol.* 24:2672–2681 (1994).

Weichhold et al., "The human immunoglobulin κ locus consists of two copies that are organized in opposite polarity." *Genomics* 16:503–511 (1993).

Yamada, M. et al., "Preferential utilization of specific immunoglobulin heavy chain diversity and joining segments in adult human peripheral blood B lymphocytes." *J. Exp. Med.* 173:395–407 (1991).

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What we claim is:

1. An isolated antibody that is capable of binding epidermal growth factor receptor comprising a heavy chain variable region comprising a contiguous sequence from CDR1 through CDR3 as represented in SEQ ID NO:23.

2. The antibody of claim 1, further comprising a light chain variable region comprising the sequence represented by SEQ ID NO:24.

3. An isolated antibody that is capable of binding epidermal growth factor receptor comprising a heavy chain variable region comprising a contiguous sequence from CDR1 through CDR3 as represented in SEQ ID NO:25.

4. The antibody of claim 3, further comprising a light chain variable region comprising the sequence represented by SEQ ID NO:26.

5. An isolated antibody that is capable of binding epidermal growth factor receptor comprising a heavy chain variable region comprising a contiguous sequence from CDR1 through CDR3 as represented in SEQ ID NO:27.

6. The antibody of claim 5, further comprising a light chain variable region comprising the sequence represented by SEQ ID NO:28.

7. An isolated antibody that is capable of binding epidermal growth factor receptor comprising a heavy chain variable region comprising a contiguous sequence from CDR1 through CDR3 as represented in SEQ ID NO:29.

8. The antibody of claim 7, further comprising a light chain variable region comprising the sequence represented by SEQ ID NO:30.

9. An isolated antibody that is capable of binding epidermal growth factor receptor comprising a heavy chain variable region comprising a contiguous sequence from CDR1 through CDR3 as represented in SEQ ID NO:31.

10. The antibody of claim 9, further comprising a light chain variable region comprising the sequence represented by SEQ ID NO:32.

11. An isolated antibody that is capable of binding epidermal growth factor receptor comprising a heavy chain variable region comprising a contiguous sequence from CDR1 through CDR3 as represented in SEQ ID NO:33.

12. The antibody of claim 11, further comprising a light chain variable region comprising the sequence represented by SEQ ID NO:34.

13. An isolated antibody that is capable of binding epidermal growth factor receptor comprising a heavy chain variable region comprising a contiguous sequence from CDR1 through CDR3 as represented in SEQ ID NO:35.

14. The antibody of claim 13 further comprising a light chain variable region comprising the sequence represented by SEQ ID NO:36.

15. An isolated antibody that is capable of binding epidermal growth factor receptor comprising a heavy chain variable region comprising a contiguous sequence from CDR1 through CDR3 as represented in SEQ ID NO:37.

16. The antibody of claim 15, further comprising a light chain variable region comprising the sequence represented by SEQ ID NO:38.

* * * * *

SEQUENCE LISTING

<160> NUMBER OF SEQ ID NOS: 49

<210> SEQ ID NO: 1
<211> LENGTH: 22
<212> TYPE: DNA
<213> ORGANISM: human

<400> SEQUENCE: 1
caggtgcagc tggagcagtc gg                              22

<210> SEQ ID NO: 2
<211> LENGTH: 24
<212> TYPE: DNA
<213> ORGANISM: human

<400> SEQUENCE: 2
gctgagggag tagagtcctg agga					24

<210> SEQ ID NO: 3
<211> LENGTH: 294
<212> TYPE: DNA
<213> ORGANISM: human

<400> SEQUENCE: 3
gtctctggtg gctccatcaa cagtggtgat tactactgga gctggatccg ccagcaccca	60 gggaagggcc tggactgcat tgggtacatc tattacagtg ggagcaccta ctacaacccg	120 tccctcaaga gtcgagttac catatcagta gacacgtcta agaatcagtt cttcctgaag	180 ctgacctctg tgactgccgc ggacacggcc gtgtattact gtgcgagatc tacggtggta	240 aatccgggt ggttcgaccc ctggggccar ggaaccctgg tcaccgtctc ctca		294

<210> SEQ ID NO: 4
<211> LENGTH: 264
<212> TYPE: DNA
<213> ORGANISM: human

<400> SEQUENCE: 4
accatcactt gccaggcgag tcaggacatt aacaactatt taaattggtt tcagcagaaa	60 ccagggaaag cccctaaggt cctgatccac gatgcatcca atttggaaac aggggccca	120 tcaaggttca gtggaagtgg atctgggaca gatttttactt tcaccatcag cggcctgcag	180 cctgaagaca ttgcaacata ttattgtcaa cagtatgaaa gtctcccact cactttcggc	240 ggagggacca aggtggagat caaa					264

<210> SEQ ID NO: 5
<211> LENGTH: 291
<212> TYPE: DNA
<213> ORGANISM: human

<400> SEQUENCE: 5
gtctctggtg gctccatcaa cagtggtgat tactactgga gctggatccg ccagcaccca	60 gggaagggcc tggagtggat tgggtccatc tattacagtg gaacaccctt ctacaacccg	120 tccctcaaga gtcgagttac catatcacta gacacgtcta agaaccagtt ctccctgaag	180 ctgagttctg tgactgccgc ggacacggcc gtgtgttact gtgcgagaaa tatagtgact	240 acgggtgctt ttgatatctg gggccaaggg acaatggtca ccgtctcttc a		291

<210> SEQ ID NO: 6
<211> LENGTH: 264
<212> TYPE: DNA
<213> ORGANISM: human

<400> SEQUENCE: 6
accatcactt gtcaggcgag tcaggacatt accatttatt taaattggta tcaacagaaa	60 ccagggaaag cccctaagct cctgatcaac gacgcatcca gtttggaaac agggtccca	120 ttaaggttca gtggaagtgg atctgggaca gatttttactt tcaccatcag cagcctgcag	180 cctgaagata ttgcaacata ttactgtcaa cagtatgatc atctcccgct cactttcggc	240

```
ggcgggacca aggtggcgat caaa                                           264
```

<210> SEQ ID NO: 7
<211> LENGTH: 288
<212> TYPE: DNA
<213> ORGANISM: human

<400> SEQUENCE: 7

```
gtctctggtg gctccatcag cagtggtgat tactactgga cctggatccg ccagcaccca    60
gggaagggcc tggagtggat tgggtacatc tattacagtg gaacaccta ctacaacccg    120
tccctcaaga gtcgagtttc catgtcaata gacacgtctg agaaccagtt ctccctgaag   180
ctgagctctg tgactgccgc ggacacggcc gtgtattact gtgcgagaaa accagtgact   240
ggggggagg actactgggg ccagggaacc ctggtcaccg tctcctca                288
```

<210> SEQ ID NO: 8
<211> LENGTH: 262
<212> TYPE: DNA
<213> ORGANISM: human

<400> SEQUENCE: 8

```
accatcactt gccaggcgag tcaggacatt agtaactatt taaattggta tcagcagaaa    60
ccagggaaag ccctaagctc ctgatctacg atgcttccaa tttggaaaca ggggtcccat   120
caaggttcag tggagtggat ctgggacaga ttttactttc accatcagca gcctgcagcc   180
tgaagatgtt ggaacatatg tctgtcaaca gtatgagagt ctcccgtgcg gttttggcca   240
ggggaccaaa ctggagatca aa                                           262
```

<210> SEQ ID NO: 9
<211> LENGTH: 291
<212> TYPE: DNA
<213> ORGANISM: human
<220> FEATURE:
<221> NAME/KEY: misc_feature
<222> LOCATION: (1)...(291)
<223> OTHER INFORMATION: n = A,T,C or G

<400> SEQUENCE: 9

```
gtctctggtg gctccatcaa cagtggtgat ttctactgga gctggatccg ccaacaccca    60
gggaagggcc tggagtggat tgggtacatc tattacagtg ggagcaccta ctacaacccg   120
tccctcaaga gtcgagttac catgtcaata gacccgtcta agaaccagtt ctccctgaaa   180
ctgatctctg tgactgccgc ggacacggcc gtttattact gtgcgacntc cctttactat   240
ggcgggggta tggacgtctg ggccaaggg accacggtca ccgtctcctc a              291
```

<210> SEQ ID NO: 10
<211> LENGTH: 264
<212> TYPE: DNA
<213> ORGANISM: human
<220> FEATURE:
<221> NAME/KEY: misc_feature
<222> LOCATION: (1)...(264)
<223> OTHER INFORMATION: n = A,T,C or G

<400> SEQUENCE: 10

```
accatcactt gccaggcgag tcaggacatt aacaactatt tgaattggta tcagcagagg    60
ccngggaacg cccctaaaact cctgatctac gatgcatcca atttgaaaac agggtccca   120
tcaaggttca gtggaagtgg atctgggaca gatttttact tcaccatcaa cagcctgcag   180
```

```
cctgaagata ttgcgacata ttattgtcaa cactatgatc atctcccgtg gacgttcggc    240
caagggacca aggtggaant caaa                                            264

<210> SEQ ID NO: 11
<211> LENGTH: 291
<212> TYPE: DNA
<213> ORGANISM: human

<400> SEQUENCE: 11
gtctctggtg gctccatcaa caatggtgat tactactgga gctggatccg ccagcaccca     60
gggaagggcc tggagtggat tgggcacatc tattacagtg ggagcaccta ctacatcccg    120
tccctcaaga gtcgaactac catatcagta gacacgtcta agaaccagtt ctccctgaag    180
ctgaactctg tgactgccgc ggacacggcc gtgtattact gtgcgagagg gacagtaact    240
acgtactact ttgactactg gggccaggga accctggtca ccgtctcctc a             291

<210> SEQ ID NO: 12
<211> LENGTH: 270
<212> TYPE: DNA
<213> ORGANISM: human

<400> SEQUENCE: 12
accatcactt gccgggcaag tcagagcatt agcagctatt taaattggta tcagcagaaa     60
ccagggaaag cccctaagct cctgatctat gctgcatcca gtttgcaaag tggggtccca    120
tcaaggttca gtggcagtgg atctgggaca gatttcactc tcaccatcag cagtctgcaa    180
cctgaagatt ttgcaactta ctactgtcaa caggttacag aacccctcc  ggagtgcagt    240 tttggccagg gaccaagct  ggagatcaaa                                      270

<210> SEQ ID NO: 13
<211> LENGTH: 291
<212> TYPE: DNA
<213> ORGANISM: human

<400> SEQUENCE: 13
gtctctggtg gctccgtcag cagtggtgat tactactgga gctggatccg gcagccccca     60
gggaagggac tggagtggat tggacatctc tattacagtg gaacaccaa ctacaacccc    120 tccctcaaga gtcgagtcac catatcatta gacacgtcca agaaccagtt ctccctgaag    180
ctgagctctg tgaccgctgc ggacacggcc gtgtattact gtgcgagaga ttttttgact    240
ggttccttct ttgactactg gggccaggga accctggtca ccgtctcctc a             291

<210> SEQ ID NO: 14
<211> LENGTH: 264
<212> TYPE: DNA
<213> ORGANISM: human

<400> SEQUENCE: 14
accatcactt gccaggcgag tcaggacata agcaactatt taaattggta tcagcagaaa     60
ccagggaaag cccctaagct cctgatcaac gatgcatccg atttggaaac aggggtccca    120
tcaaggatca gtggaagtgg atctgggaca gattttactt tcaccatcag caacctgcag    180
cctgaagata ttgcaacata ttactgtcaa caatatgata gtctcccgct cactttcggc    240
ggagggacca aggtggagat caga                                            264

<210> SEQ ID NO: 15
<211> LENGTH: 288
```

```
<212> TYPE: DNA
<213> ORGANISM: human

<400> SEQUENCE: 15
gtctctggtg gctccgtcta cagtggtgat tactactgga gctggatccg gcagccccca      60
gggaagggac tggagtggat tgggtatatc tattacagtg ggagcaccaa ttacaatccc     120
tccctcaaga gtcgagtcac catatcagta gacacgtcca agaaccagtt ctccctgaag     180
ctgagctctg tgaccgctgc ggacacggcc gtgtattact gtgcgagaga ctccatactg     240
ggagctacca actactgggg ccagggaacc ctggtcaccg tctcctca                   288

<210> SEQ ID NO: 16
<211> LENGTH: 264
<212> TYPE: DNA
<213> ORGANISM: human
<220> FEATURE:
<221> NAME/KEY: misc_feature
<222> LOCATION: (1)...(264)
<223> OTHER INFORMATION: n = A,T,C or G

<400> SEQUENCE: 16
accatcactt gccaggcgag tcnggacatt aataactatt tanattggtn tcagcagaaa      60
ccagggaaag cccctaaast cctgatctcc gatgcatcca atttagaaac aggggtccca     120
tcgaggttca gtggaagtgg atctgggaca gantntactt tcaccatcag cagcctgcag     180
cctgaagata ttgcnacata tcactgtcna cagtatnata gtctcccgct cactttcggc     240
ggagggacca agtagagat caaa                                              264

<210> SEQ ID NO: 17
<211> LENGTH: 288
<212> TYPE: DNA
<213> ORGANISM: human

<400> SEQUENCE: 17
gtctctggtg gctccgtcag cagtggtgat tactactgga cctggatccg gcagtcccca      60
gggaagggac tggagtggat tggacacatc tattacagtg ggaacaccaa ttataacccc     120
tccctcaaga gtcgactcac catatcaatt gacacgtcca agactcagtt ctccctgaag     180
ctgagttctg tgaccgctgc ggacacggcc atttattact gtgtgcgaga tcgagtgact     240
ggtgcttttg atatctgggg ccaagggaca atggtcaccg tctcttca                   288

<210> SEQ ID NO: 18
<211> LENGTH: 264
<212> TYPE: DNA
<213> ORGANISM: human

<400> SEQUENCE: 18
accatcactt gccaggcgag tcaggacatc agcaactatt taaattggta tcagcagaaa      60
ccagggaaag cccctaaact cctgatctac gatgcatcca atttggaaac aggggtccca     120
tcaaggttca gtggaagtgg atctgggaca gattttactt tcaccatcag cagcctgcag     180
cctgaagata ttgcaacata tttctgtcaa cactttgatc atctcccgct cgctttcggc     240
ggagggacca agtgggagat caaa                                             264

<210> SEQ ID NO: 19
<211> LENGTH: 76
<212> TYPE: PRT
<213> ORGANISM: human
```

```
<400> SEQUENCE: 19

Val Ser Gly Gly Ser Ile Ser Gly Gly Tyr Tyr Trp Ser Trp Ile
 1               5                  10                  15

Arg Gln His Pro Gly Lys Gly Leu Glu Trp Ile Gly Tyr Ile Tyr Tyr
             20                  25                  30

Ser Gly Ser Thr Tyr Tyr Asn Pro Ser Leu Lys Ser Arg Val Thr Ile
             35                  40                  45

Ser Val Asp Thr Ser Lys Asn Gln Phe Ser Leu Lys Leu Ser Ser Val
         50                  55                  60

Thr Ala Ala Asp Thr Ala Val Tyr Tyr Cys Ala Arg
65                  70                  75

<210> SEQ ID NO: 20
<211> LENGTH: 76
<212> TYPE: PRT
<213> ORGANISM: human

<400> SEQUENCE: 20

Thr Ile Thr Cys Gln Ala Ser Gln Asp Ile Ser Asn Tyr Leu Asn Trp
 1               5                  10                  15

Tyr Gln Gln Lys Pro Gly Lys Ala Pro Lys Leu Leu Ile Tyr Asp Ala
             20                  25                  30

Ser Asn Leu Glu Thr Gly Val Pro Ser Arg Phe Ser Gly Ser Gly Ser
             35                  40                  45

Gly Thr Asp Phe Thr Phe Thr Ile Ser Ser Leu Gln Pro Glu Asp Ile
         50                  55                  60

Ala Thr Tyr Tyr Cys Gln Gln Tyr Asp Asn Leu Pro
65                  70                  75

<210> SEQ ID NO: 21
<211> LENGTH: 76
<212> TYPE: PRT
<213> ORGANISM: human

<400> SEQUENCE: 21

Thr Ile Thr Cys Arg Ala Ser Gln Ser Ile Ser Ser Tyr Leu Asn Trp
 1               5                  10                  15

Tyr Gln Gln Lys Pro Gly Lys Ala Pro Lys Leu Leu Ile Tyr Ala Ala
             20                  25                  30

Ser Ser Leu Gln Ser Gly Val Pro Ser Arg Phe Ser Gly Ser Gly Ser
             35                  40                  45

Gly Thr Asp Phe Thr Leu Thr Ile Ser Ser Leu Gln Pro Glu Asp Phe
         50                  55                  60

Ala Thr Tyr Tyr Cys Gln Gln Ser Tyr Ser Thr Pro
65                  70                  75

<210> SEQ ID NO: 22
<211> LENGTH: 76
<212> TYPE: PRT
<213> ORGANISM: human

<400> SEQUENCE: 22

Val Ser Gly Gly Ser Val Ser Gly Ser Tyr Tyr Trp Ser Trp Ile
 1               5                  10                  15

Arg Gln Pro Pro Gly Lys Gly Leu Glu Trp Ile Gly Tyr Ile Tyr Tyr
             20                  25                  30

Ser Gly Ser Thr Asn Tyr Asn Pro Ser Leu Lys Ser Arg Val Thr Ile
             35                  40                  45
```

```
Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg
65                  70                  75
```

<210> SEQ ID NO: 23
<211> LENGTH: 98
<212> TYPE: PRT
<213> ORGANISM: human

<400> SEQUENCE: 23

```
Val Ser Gly Gly Ser Ile Asn Ser Gly Asp Tyr Tyr Trp Ser Trp Ile
1               5                   10                  15

Arg Gln His Pro Gly Lys Gly Leu Asp Cys Ile Gly Tyr Ile Tyr Tyr
                20                  25                  30

Ser Gly Ser Thr Tyr Tyr Asn Pro Ser Leu Lys Ser Arg Val Thr Ile
            35                  40                  45

Ser Val Asp Thr Ser Lys Asn Gln Phe Phe Leu Lys Leu Thr Ser Val
    50                  55                  60

Thr Ala Ala Asp Thr Ala Val Tyr Tyr Cys Ala Arg Ser Thr Val Val
65                  70                  75                  80

Asn Pro Gly Trp Phe Asp Pro Trp Gly Gln Gly Thr Leu Val Thr Val
                85                  90                  95

Ser Ser
```

<210> SEQ ID NO: 24
<211> LENGTH: 105
<212> TYPE: PRT
<213> ORGANISM: human

<400> SEQUENCE: 24

```
Thr Ile Thr Cys Gln Ala Ser Gln Asp Ile Asn Asn Tyr Leu Asn Trp
1               5                   10                  15

Phe Gln Gln Lys Pro Gly Lys Ala Pro Lys Val Leu Ile His Asp Ala
                20                  25                  30

Ser Asn Leu Glu Thr Gly Gly Pro Ser Arg Phe Ser Gly Ser Gly Ser
            35                  40                  45

Gly Thr Asp Phe Thr Phe Thr Ile Ser Gly Leu Gln Pro Glu Asp Ile
    50                  55                  60

Ala Thr Tyr Tyr Cys Gln Gln Tyr Glu Ser Leu Pro Leu Thr Phe Gly
65                  70                  75                  80

Gly Gly Thr Lys Val Glu Ile Lys Arg Thr Val Ala Ala Pro Ser Val
                85                  90                  95

Phe Ile Phe Pro Pro Ser Asp Glu Gln
                100                 105
```

<210> SEQ ID NO: 25
<211> LENGTH: 97
<212> TYPE: PRT
<213> ORGANISM: human

<400> SEQUENCE: 25

```
Val Ser Gly Gly Ser Ile Asn Ser Gly Asp Tyr Tyr Trp Ser Trp Ile
1               5                   10                  15

Arg Gln His Pro Gly Lys Gly Leu Glu Trp Ile Gly Ser Ile Tyr Tyr
                20                  25                  30

Ser Gly Asn Thr Phe Tyr Asn Pro Ser Leu Lys Ser Arg Val Thr Ile
```

```
                35                  40                  45
Ser Leu Asp Thr Ser Lys Asn Gln Phe Ser Leu Lys Leu Ser Ser Val
    50                  55                  60
Thr Ala Ala Asp Thr Ala Val Cys Tyr Cys Ala Arg Asn Ile Val Thr
65                  70                  75                  80
Thr Gly Ala Phe Asp Ile Trp Gly Gln Gly Thr Met Val Thr Val Ser
                85                  90                  95
Ser
```

```
<210> SEQ ID NO: 26
<211> LENGTH: 105
<212> TYPE: PRT
<213> ORGANISM: human

<400> SEQUENCE: 26

Thr Ile Thr Cys Gln Ala Ser Gln Asp Ile Thr Ile Tyr Leu Asn Trp
1               5                   10                  15
Tyr Gln Gln Lys Pro Gly Lys Ala Pro Lys Leu Leu Ile Asn Asp Ala
                20                  25                  30
Ser Ser Leu Glu Thr Gly Val Pro Leu Arg Phe Ser Gly Ser Gly Ser
            35                  40                  45
Gly Thr Asp Phe Thr Phe Thr Ile Ser Ser Leu Gln Pro Glu Asp Ile
    50                  55                  60
Ala Thr Tyr Tyr Cys Gln Gln Tyr Asp His Leu Pro Leu Thr Phe Gly
65                  70                  75                  80
Gly Gly Thr Lys Val Ala Ile Lys Arg Thr Val Ala Ala Pro Ser Val
                85                  90                  95
Phe Ile Phe Pro Pro Ser Asp Glu Gln
                100                 105
```

```
<210> SEQ ID NO: 27
<211> LENGTH: 96
<212> TYPE: PRT
<213> ORGANISM: human

<400> SEQUENCE: 27

Val Ser Gly Gly Ser Ile Ser Ser Gly Asp Tyr Tyr Trp Thr Trp Ile
1               5                   10                  15
Arg Gln His Pro Gly Lys Gly Leu Glu Trp Ile Gly Tyr Ile Tyr Tyr
                20                  25                  30
Ser Gly Asn Thr Tyr Tyr Asn Pro Ser Leu Lys Ser Arg Val Ser Met
            35                  40                  45
Ser Ile Asp Thr Ser Glu Asn Gln Phe Ser Leu Lys Leu Ser Ser Val
    50                  55                  60
Thr Ala Ala Asp Thr Ala Val Tyr Tyr Cys Ala Arg Lys Pro Val Thr
65                  70                  75                  80
Gly Gly Glu Asp Tyr Trp Gly Gln Gly Thr Leu Val Thr Val Ser Ser
                85                  90                  95
```

```
<210> SEQ ID NO: 28
<211> LENGTH: 105
<212> TYPE: PRT
<213> ORGANISM: human

<400> SEQUENCE: 28

Thr Ile Thr Cys Gln Ala Ser Gln Asp Ile Ser Asn Tyr Leu Asn Trp
1               5                   10                  15
```

```
Tyr Gln Gln Lys Pro Gly Lys Ala Pro Lys Leu Leu Ile Tyr Asp Ala
                20                  25                  30

Ser Asn Leu Glu Thr Gly Val Pro Ser Arg Phe Ser Gly Ser Gly Ser
            35                  40                  45

Gly Thr Asp Phe Thr Phe Thr Ile Ser Ser Leu Gln Pro Glu Asp Ile
        50                  55                  60

Val Gly Tyr Tyr Val Gln Gln Tyr Glu Ser Leu Pro Cys Gly Phe Gly
65                  70                  75                  80

Gln Gly Thr Lys Leu Glu Ile Lys Arg Thr Val Ala Ala Pro Ser Val
                85                  90                  95

Phe Ile Phe Pro Pro Ser Asp Glu Gln
                100                 105

<210> SEQ ID NO: 29
<211> LENGTH: 97
<212> TYPE: PRT
<213> ORGANISM: human

<400> SEQUENCE: 29

Val Ser Gly Gly Ser Ile Asn Ser Gly Asp Phe Tyr Trp Ser Trp Ile
1               5                   10                  15

Arg Gln His Pro Gly Lys Gly Leu Glu Trp Ile Gly Tyr Ile Tyr Tyr
                20                  25                  30

Ser Gly Ser Thr Tyr Tyr Asn Pro Ser Leu Lys Ser Arg Val Thr Met
            35                  40                  45

Ser Ile Asp Pro Ser Lys Asn Gln Phe Ser Leu Lys Leu Ile Ser Val
        50                  55                  60

Thr Ala Ala Asp Thr Ala Val Tyr Tyr Cys Ala Thr Ser Leu Tyr Tyr
65                  70                  75                  80

Gly Gly Gly Met Asp Val Trp Gly Gln Gly Thr Thr Val Thr Val Ser
                85                  90                  95

Ser

<210> SEQ ID NO: 30
<211> LENGTH: 105
<212> TYPE: PRT
<213> ORGANISM: human
<220> FEATURE:
<221> NAME/KEY: VARIANT
<222> LOCATION: (1)...(105)
<223> OTHER INFORMATION: Xaa = Any Amino Acid

<400> SEQUENCE: 30

Thr Ile Thr Cys Gln Ala Ser Gln Asp Ile Ser Asn Asn Leu Asn Trp
1               5                   10                  15

Tyr Gln Gln Lys Arg Gly Asn Ala Pro Lys Leu Leu Ile Tyr Asp Ala
                20                  25                  30

Ser Asn Leu Glu Thr Gly Val Pro Ser Arg Phe Ser Gly Ser Gly Ser
            35                  40                  45

Gly Thr Asp Phe Thr Phe Thr Ile Ser Asn Leu Gln Pro Glu Asp Ile
        50                  55                  60

Ala Thr Tyr Tyr Cys Gln His Tyr Asp His Leu Pro Trp Thr Phe Gly
65                  70                  75                  80

Gln Gly Thr Lys Val Glu Xaa Lys Arg Thr Val Ala Ala Pro Ser Val
                85                  90                  95

Phe Ile Phe Pro Pro Ser Asp Glu Gln
                100                 105
```

<210> SEQ ID NO: 31
<211> LENGTH: 97
<212> TYPE: PRT
<213> ORGANISM: human

<400> SEQUENCE: 31

Val Ser Gly Gly Ser Ile Asn Asn Gly Asp Tyr Tyr Trp Ser Trp Ile
1               5                   10                  15

Arg Gln His Pro Gly Lys Gly Leu Glu Trp Ile Gly His Ile Tyr Tyr
                20                  25                  30

Ser Gly Ser Thr Tyr Tyr Ile Pro Ser Leu Lys Ser Arg Thr Thr Ile
            35                  40                  45

Ser Val Asp Thr Ser Lys Asn Gln Phe Ser Leu Lys Leu Asn Ser Val
50                  55                  60

Thr Ala Ala Asp Thr Ala Val Tyr Tyr Cys Ala Arg Gly Thr Val Thr
65                  70                  75                  80

Thr Tyr Tyr Phe Asp Tyr Trp Gly Gln Gly Thr Thr Val Thr Val Ser
                85                  90                  95

Ser

<210> SEQ ID NO: 32
<211> LENGTH: 107
<212> TYPE: PRT
<213> ORGANISM: human

<400> SEQUENCE: 32

Thr Ile Thr Cys Arg Ala Ser Gln Ser Ile Ser Ser Tyr Leu Asn Trp
1               5                   10                  15

Tyr Gln Gln Lys Pro Gly Lys Ala Pro Lys Leu Leu Ile Tyr Ala Ala
                20                  25                  30

Ser Ser Leu Gln Ser Gly Val Pro Ser Arg Phe Ser Gly Ser Gly Ser
            35                  40                  45

Gly Thr Asp Phe Thr Leu Thr Ile Ser Ser Leu Gln Pro Glu Asp Phe
50                  55                  60

Ala Thr Tyr Tyr Cys Gln Gln Gly Tyr Arg Thr Pro Pro Glu Cys Ser
65                  70                  75                  80

Phe Gly Gln Gly Thr Lys Leu Glu Ile Lys Arg Thr Val Ala Ala Pro
                85                  90                  95

Ser Val Phe Ile Phe Pro Pro Ser Asp Glu Gln
            100                 105

<210> SEQ ID NO: 33
<211> LENGTH: 97
<212> TYPE: PRT
<213> ORGANISM: human

<400> SEQUENCE: 33

Val Ser Gly Gly Ser Val Ser Ser Gly Asp Tyr Tyr Trp Ser Trp Ile
1               5                   10                  15

Arg Gln Pro Pro Gly Lys Gly Leu Glu Trp Ile Gly His Leu Tyr Tyr
                20                  25                  30

Ser Gly Asn Thr Asn Tyr Asn Pro Ser Leu Lys Ser Arg Val Thr Ile
            35                  40                  45

Ser Leu Asp Thr Ser Lys Asn Gln Phe Ser Leu Lys Leu Ser Ser Val
50                  55                  60

Thr Ala Ala Asp Thr Ala Val Tyr Tyr Cys Ala Arg Asp Phe Leu Thr
65                  70                  75                  80

```
Gly Ser Phe Phe Asp Tyr Trp Gly Gln Gly Thr Leu Val Thr Val Ser
                85                  90                  95
Ser

<210> SEQ ID NO: 34
<211> LENGTH: 105
<212> TYPE: PRT
<213> ORGANISM: human

<400> SEQUENCE: 34

Thr Ile Thr Cys Gln Ala Ser Gln Asp Ile Ser Asn Tyr Leu Asn Trp
  1               5                  10                  15

Tyr Gln Gln Lys Pro Gly Lys Ala Pro Lys Leu Leu Ile Asn Asp Ala
                20                  25                  30

Ser Asp Leu Glu Thr Gly Val Pro Ser Arg Ile Ser Gly Ser Gly Ser
                35                  40                  45

Gly Thr Asp Phe Thr Phe Thr Ile Ser Asn Leu Gln Pro Glu Asp Ile
             50                  55                  60

Ala Thr Tyr Tyr Cys Gln Gln Tyr Asp Ser Leu Pro Leu Thr Phe Gly
 65                  70                  75                  80

Gly Gly Thr Lys Val Glu Ile Arg Arg Thr Val Ala Ala Pro Ser Val
                85                  90                  95

Phe Ile Phe Pro Pro Ser Asp Glu Gln
                100                 105

<210> SEQ ID NO: 35
<211> LENGTH: 96
<212> TYPE: PRT
<213> ORGANISM: human

<400> SEQUENCE: 35

Val Ser Gly Gly Ser Val Tyr Ser Gly Asp Tyr Tyr Trp Ser Trp Ile
  1               5                  10                  15

Arg Gln Pro Pro Gly Lys Gly Leu Glu Trp Ile Gly Tyr Ile Tyr Tyr
                20                  25                  30

Ser Gly Ser Thr Asn Tyr Asn Pro Ser Leu Lys Ser Arg Val Thr Ile
                35                  40                  45

Ser Val Asp Thr Ser Lys Asn Gln Phe Ser Leu Lys Leu Ser Ser Val
             50                  55                  60

Thr Ala Ala Asp Thr Ala Val Tyr Tyr Cys Ala Arg Asp Ser Ile Leu
 65                  70                  75                  80

Gly Ala Thr Asn Tyr Trp Gly Gln Gly Thr Leu Val Thr Val Ser Ser
                85                  90                  95

<210> SEQ ID NO: 36
<211> LENGTH: 105
<212> TYPE: PRT
<213> ORGANISM: human
<220> FEATURE:
<221> NAME/KEY: VARIANT
<222> LOCATION: (1)...(105)
<223> OTHER INFORMATION: Xaa = Any Amino Acid

<400> SEQUENCE: 36

Thr Ile Thr Cys Gln Ala Ser Gln Xaa Ile Ser Asn Tyr Leu Xaa Trp
  1               5                  10                  15

Tyr Gln Gln Lys Pro Gly Lys Ala Pro Lys Xaa Leu Ile Ser Asp Ala
                20                  25                  30
```

```
Ser Asn Leu Glu Thr Gly Val Pro Ser Arg Phe Ser Gly Ser Gly Ser
         35                  40                  45

Gly Thr Xaa Xaa Thr Phe Thr Ile Ser Leu Gln Pro Glu Asp Ile
         50                  55                  60

Ala Thr Tyr His Cys Xaa Gln Tyr Xaa Ser Leu Pro Leu Thr Phe Gly
 65                  70                  75                  80

Gly Gly Thr Lys Val Glu Ile Lys Arg Thr Val Ala Ala Pro Ser Val
                 85                  90                  95

Phe Ile Phe Pro Pro Ser Asp Glu Gln
                100                 105

<210> SEQ ID NO: 37
<211> LENGTH: 95
<212> TYPE: PRT
<213> ORGANISM: human

<400> SEQUENCE: 37

Val Ser Gly Gly Ser Val Ser Ser Gly Asp Tyr Tyr Trp Thr Trp Ile
 1               5                  10                  15

Arg Gln Ser Pro Gly Lys Gly Leu Glu Trp Ile Gly His Ile Tyr Tyr
                 20                  25                  30

Ser Gly Asn Thr Asn Tyr Asn Pro Ser Leu Lys Ser Arg Leu Thr Ile
         35                  40                  45

Ser Ile Asp Thr Ser Lys Thr Gln Phe Ser Leu Lys Leu Ser Ser Val
         50                  55                  60

Thr Ala Ala Asp Thr Ala Ile Tyr Tyr Cys Val Arg Asp Arg Val Thr
 65                  70                  75                  80

Gly Ala Phe Asp Ile Trp Gly Gln Gly Thr Met Val Thr Ser Ser
                 85                  90                  95

<210> SEQ ID NO: 38
<211> LENGTH: 105
<212> TYPE: PRT
<213> ORGANISM: human

<400> SEQUENCE: 38

Thr Ile Thr Cys Gln Ala Ser Gln Asp Ile Ser Asn Tyr Leu Asn Trp
 1               5                  10                  15

Tyr Gln Gln Lys Pro Gly Lys Ala Pro Lys Leu Leu Ile Tyr Asp Ala
                 20                  25                  30

Ser Asn Leu Glu Thr Gly Val Pro Ser Arg Phe Ser Gly Ser Gly Ser
         35                  40                  45

Gly Thr Asp Phe Thr Phe Thr Ile Ser Ser Leu Gln Pro Glu Asp Ile
         50                  55                  60

Ala Thr Tyr Phe Cys Gln His Phe Asp His Leu Pro Leu Ala Phe Gly
 65                  70                  75                  80

Gly Gly Thr Lys Val Glu Ile Lys Arg Thr Val Ala Ala Pro Ser Val
                 85                  90                  95

Phe Ile Phe Pro Pro Ser Asp Glu Gln
                100                 105

<210> SEQ ID NO: 39
<211> LENGTH: 8
<212> TYPE: DNA
<213> ORGANISM: human
<220> FEATURE:
<221> NAME/KEY: misc_feature
<222> LOCATION: (1)...(8)
<223> OTHER INFORMATION: n = A,T,C or G
```

-continued

```
<400> SEQUENCE: 39 cntccctt                                                                    8

<210> SEQ ID NO: 40
<211> LENGTH: 21
<212> TYPE: PRT
<213> ORGANISM: human

<400> SEQUENCE: 40

Ala Ser Thr Lys Gly Pro Ser Val Phe Pro Pro Leu Ala Pro Cys Ser
 1               5                  10                  15

Arg Ser Thr Ser Thr
             20

<210> SEQ ID NO: 41
<211> LENGTH: 17
<212> TYPE: PRT
<213> ORGANISM: human

<400> SEQUENCE: 41

Arg Thr Val Ala Ala Pro Ser Val Phe Ile Phe Pro Pro Ser Asp Glu
 1               5                  10                  15

Gln

<210> SEQ ID NO: 42
<211> LENGTH: 119
<212> TYPE: PRT
<213> ORGANISM: human

<400> SEQUENCE: 42

Val Ser Gly Gly Ser Ile Asn Ser Gly Asp Tyr Tyr Trp Ser Trp Ile
 1               5                  10                  15

Arg Gln His Pro Gly Lys Gly Leu Asp Cys Ile Gly Tyr Ile Tyr Tyr
             20                  25                  30

Ser Gly Ser Thr Tyr Tyr Asn Pro Ser Leu Lys Ser Arg Val Thr Ile
         35                  40                  45

Ser Val Asp Thr Ser Lys Asn Gln Phe Phe Leu Lys Leu Thr Ser Val
     50                  55                  60

Thr Ala Ala Asp Thr Ala Val Tyr Tyr Cys Ala Arg Ser Thr Val Val
65                  70                  75                  80

Asn Pro Gly Trp Phe Asp Pro Trp Gly Gln Gly Thr Leu Val Thr Val
                 85                  90                  95

Ser Ser Ala Ser Thr Lys Gly Pro Ser Val Phe Pro Pro Leu Ala Pro
            100                 105                 110

Cys Ser Arg Ser Thr Ser Thr
            115

<210> SEQ ID NO: 43
<211> LENGTH: 118
<212> TYPE: PRT
<213> ORGANISM: human

<400> SEQUENCE: 43

Val Ser Gly Gly Ser Ile Asn Ser Gly Asp Tyr Tyr Trp Ser Trp Ile
 1               5                  10                  15

Arg Gln His Pro Gly Lys Gly Leu Glu Trp Ile Gly Ser Ile Tyr Tyr
             20                  25                  30

Ser Gly Asn Thr Phe Tyr Asn Pro Ser Leu Lys Ser Arg Val Thr Ile
```

```
                35                  40                  45
Ser Leu Asp Thr Ser Lys Asn Gln Phe Ser Leu Lys Leu Ser Ser Val
         50                  55                  60
Thr Ala Ala Asp Thr Ala Val Cys Tyr Cys Ala Arg Asn Ile Val Thr
 65                  70                  75                  80
Thr Gly Ala Phe Asp Ile Trp Gly Gln Gly Thr Met Val Thr Val Ser
                 85                  90                  95
Ser Ala Ser Thr Lys Gly Pro Ser Val Phe Pro Pro Leu Ala Pro Cys
                100                 105                 110
Ser Arg Ser Thr Ser Thr
            115
```

<210> SEQ ID NO: 44
<211> LENGTH: 117
<212> TYPE: PRT
<213> ORGANISM: human

<400> SEQUENCE: 44

```
Val Ser Gly Gly Ser Ile Ser Ser Gly Asp Tyr Tyr Trp Thr Trp Ile
 1               5                  10                  15
Arg Gln His Pro Gly Lys Gly Leu Glu Trp Ile Gly Tyr Ile Tyr Tyr
                 20                  25                  30
Ser Gly Asn Thr Tyr Tyr Asn Pro Ser Leu Lys Ser Arg Val Ser Met
                 35                  40                  45
Ser Ile Asp Thr Ser Glu Asn Gln Phe Ser Leu Lys Leu Ser Ser Val
         50                  55                  60
Thr Ala Ala Asp Thr Ala Val Tyr Tyr Cys Ala Arg Lys Pro Val Thr
 65                  70                  75                  80
Gly Gly Glu Asp Tyr Trp Gly Gln Gly Thr Leu Val Thr Val Ser Ser
                 85                  90                  95
Ala Ser Thr Lys Gly Pro Ser Val Phe Pro Pro Leu Ala Pro Cys Ser
                100                 105                 110
Arg Ser Thr Ser Thr
            115
```

<210> SEQ ID NO: 45
<211> LENGTH: 118
<212> TYPE: PRT
<213> ORGANISM: human

<400> SEQUENCE: 45

```
Val Ser Gly Gly Ser Ile Asn Ser Gly Asp Phe Tyr Trp Ser Trp Ile
 1               5                  10                  15
Arg Gln His Pro Gly Lys Gly Leu Glu Trp Ile Gly Tyr Ile Tyr Tyr
                 20                  25                  30
Ser Gly Ser Thr Tyr Tyr Asn Pro Ser Leu Lys Ser Arg Val Thr Met
                 35                  40                  45
Ser Ile Asp Pro Ser Lys Asn Gln Phe Ser Leu Lys Leu Ile Ser Val
         50                  55                  60
Thr Ala Ala Asp Thr Ala Val Tyr Tyr Cys Ala Thr Ser Leu Tyr Tyr
 65                  70                  75                  80
Gly Gly Gly Met Asp Val Trp Gly Gln Gly Thr Thr Val Thr Val Ser
                 85                  90                  95
Ser Ala Ser Thr Lys Gly Pro Ser Val Phe Pro Pro Leu Ala Pro Cys
                100                 105                 110
Ser Arg Ser Thr Ser Thr
```

```
                115

<210> SEQ ID NO: 46
<211> LENGTH: 118
<212> TYPE: PRT
<213> ORGANISM: human

<400> SEQUENCE: 46

Val Ser Gly Gly Ser Ile Asn Asn Gly Asp Tyr Tyr Trp Ser Trp Ile
1               5                   10                  15

Arg Gln His Pro Gly Lys Gly Leu Glu Trp Ile Gly His Ile Tyr Tyr
            20                  25                  30

Ser Gly Ser Thr Tyr Tyr Ile Pro Ser Leu Lys Ser Arg Thr Thr Ile
        35                  40                  45

Ser Val Asp Thr Ser Lys Asn Gln Phe Ser Leu Lys Leu Asn Ser Val
    50                  55                  60

Thr Ala Ala Asp Thr Ala Val Tyr Tyr Cys Ala Arg Gly Thr Val Thr
65                  70                  75                  80

Thr Tyr Tyr Phe Asp Tyr Trp Gly Gln Gly Thr Thr Val Thr Val Ser
                85                  90                  95

Ser Ala Ser Thr Lys Gly Pro Ser Val Phe Pro Pro Leu Ala Pro Cys
            100                 105                 110

Ser Arg Ser Thr Ser Thr
            115

<210> SEQ ID NO: 47
<211> LENGTH: 118
<212> TYPE: PRT
<213> ORGANISM: human

<400> SEQUENCE: 47

Val Ser Gly Gly Ser Val Ser Ser Gly Asp Tyr Tyr Trp Ser Trp Ile
1               5                   10                  15

Arg Gln Pro Pro Gly Lys Gly Leu Glu Trp Ile Gly His Leu Tyr Tyr
            20                  25                  30

Ser Gly Asn Thr Asn Tyr Asn Pro Ser Leu Lys Ser Arg Val Thr Ile
        35                  40                  45

Ser Leu Asp Thr Ser Lys Asn Gln Phe Ser Leu Lys Leu Ser Ser Val
    50                  55                  60

Thr Ala Ala Asp Thr Ala Val Tyr Tyr Cys Ala Arg Asp Phe Leu Thr
65                  70                  75                  80

Gly Ser Phe Phe Asp Tyr Trp Gly Gln Gly Thr Leu Val Thr Val Ser
                85                  90                  95

Ser Ala Ser Thr Lys Gly Pro Ser Val Phe Pro Pro Leu Ala Pro Cys
            100                 105                 110

Ser Arg Ser Thr Ser Thr
            115

<210> SEQ ID NO: 48
<211> LENGTH: 117
<212> TYPE: PRT
<213> ORGANISM: human

<400> SEQUENCE: 48

Val Ser Gly Gly Ser Val Tyr Ser Gly Asp Tyr Tyr Trp Ser Trp Ile
1               5                   10                  15

Arg Gln Pro Pro Gly Lys Gly Leu Glu Trp Ile Gly Tyr Ile Tyr Tyr
            20                  25                  30
```

```
Ser Gly Ser Thr Asn Tyr Asn Pro Ser Leu Lys Ser Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg Asp Ser Ile Leu
65                  70                  75                  80

Gly Ala Thr Asn Tyr Trp Gly Gln Gly Thr Leu Val Thr Val Ser Ser
            85                  90                  95

Ala Ser Thr Lys Gly Pro Ser Val Phe Pro Pro Leu Ala Pro Cys Ser
            100                 105                 110

Arg Ser Thr Ser Thr
        115

<210> SEQ ID NO: 49
<211> LENGTH: 116
<212> TYPE: PRT
<213> ORGANISM: human

<400> SEQUENCE: 49

Val Ser Gly Gly Ser Val Ser Ser Gly Asp Tyr Tyr Trp Thr Trp Ile
1               5                   10                  15

Arg Gln Ser Pro Gly Lys Gly Leu Glu Trp Ile Gly His Ile Tyr Tyr
            20                  25                  30

Ser Gly Asn Thr Asn Tyr Asn Pro Ser Leu Lys Ser Arg Leu Thr Ile
        35                  40                  45

Ser Ile Asp Thr Ser Lys Thr Gln Phe Ser Leu Lys Leu Ser Ser Val
    50                  55                  60

Thr Ala Ala Asp Thr Ala Ile Tyr Tyr Cys Val Arg Asp Arg Val Thr
65                  70                  75                  80

Gly Ala Phe Asp Ile Trp Gly Gln Gly Thr Met Val Thr Ser Ser Ala
            85                  90                  95

Ser Thr Lys Gly Pro Ser Val Phe Pro Pro Leu Ala Pro Cys Ser Arg
            100                 105                 110

Ser Thr Ser Thr
        115
```